(12) United States Patent
Suh et al.

(10) Patent No.: US 10,316,061 B2
(45) Date of Patent: Jun. 11, 2019

(54) SYNTHESIS OF CELL PENETRATING PEPTIDES FOR DRUG DELIVERY AND STEM CELL APPLICATIONS

(71) Applicant: Temple University-Of The Commonwealth System of Higher Education, Philadelphia, PA (US)

(72) Inventors: Won Hyuk Suh, Blue Bell, PA (US); Geunwoo Jin, Wynnewood, PA (US)

(73) Assignee: TEMPLE UNIVERSITY OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 15/515,416

(22) PCT Filed: Oct. 2, 2015

(86) PCT No.: PCT/US2015/053722
§ 371 (c)(1),
(2) Date: Jun. 16, 2017

(87) PCT Pub. No.: WO2016/054510
PCT Pub. Date: Apr. 7, 2016

(65) Prior Publication Data
US 2017/0349628 A1 Dec. 7, 2017

Related U.S. Application Data

(60) Provisional application No. 62/058,796, filed on Oct. 2, 2014.

(51) Int. Cl.
| | |
|---|---|
| *A61K 38/08* | (2019.01) |
| *A61K 38/10* | (2006.01) |
| *A61K 38/00* | (2006.01) |
| *A61K 47/64* | (2017.01) |
| *C07K 7/00* | (2006.01) |
| *C07K 7/08* | (2006.01) |
| *C07K 7/06* | (2006.01) |
| *A61K 9/107* | (2006.01) |
| *A61K 31/203* | (2006.01) |
| *A61K 31/519* | (2006.01) |
| *C12N 5/0793* | (2010.01) |

(52) U.S. Cl.
CPC ............. *C07K 7/06* (2013.01); *A61K 9/107* (2013.01); *A61K 31/203* (2013.01); *A61K 31/519* (2013.01); *A61K 38/08* (2013.01); *A61K 47/64* (2017.08); *C12N 5/0619* (2013.01); *C07K 2319/10* (2013.01); *C07K 2319/60* (2013.01); *C12N 2501/385* (2013.01)

(58) Field of Classification Search
CPC .... A61K 31/203; A61K 31/519; A61K 38/08; A61K 38/10; A61K 38/00; A61K 47/64; A61K 9/107; C07K 7/00; C07K 7/08; C07K 2319/10; C07K 2319/60; C07K 7/06; C12N 2501/385; C12N 5/0619
USPC .... 514/1.1, 1.2, 21.3, 21.4, 21.5, 21.6, 21.7, 514/21.8; 530/300, 324, 325, 326, 327, 530/328, 329, 330
See application file for complete search history.

(56) References Cited

U.S. PATENT DOCUMENTS

| | | | |
|---|---|---|---|
| 4,522,811 A | 6/1985 | Eppstein et al. | |
| 6,663,862 B1 * | 12/2003 | Hellinga | C07K 14/31 424/130.1 |
| 8,110,238 B2 * | 2/2012 | Moine | A23L 2/60 426/546 |
| 2009/0233325 A1 | 9/2009 | Mori et al. | |
| 2009/0252847 A1 | 10/2009 | Moine | |
| 2013/0330335 A1 | 12/2013 | Bremel et al. | |
| 2014/0056811 A1 | 2/2014 | Jacob et al. | |
| 2015/0050311 A1 * | 2/2015 | Schubert | A61K 39/02 424/190.1 |

FOREIGN PATENT DOCUMENTS

| | | |
|---|---|---|
| WO | 2014041505 A1 | 3/2014 |
| WO | 2014053881 A1 | 4/2014 |

OTHER PUBLICATIONS

A0A0A9MLJ5 from UniProt, pp. 1-3. Integrated into UniProtKB/TrEMBL on Mar. 4, 2015.*
Torchilin et al., 2001, TAT peptide on the surface of liposomes affords their efficient intracellular delivery even at low temperature and in the presence of metabolic inhibitors, Proc. Natl. Acad. Sci., 98:8786-8791.
Zhang et al., 2005, Mechanism of Penetration of Antp(43-58) into Membrane Bilayers, Biochemistry, 44:10110-10118.
Nan et al., 2011, Antimicrobial activity, bactericidal mechanism and LPS-neutralizing activity of the cell-penetrating peptide pVEC and its analogs, J. Pept. Sci., 17:812-817.
Mueller et al., 2008, Comparison of Cellular Uptake Using 22 CPPs in 4 Different Cell Lines, Bioconjugate Chem., 19(12):2363-2374.
El-Andaloussi et al., 2007, Cargo-dependent cytotoxicity and delivery efficacy of cell-penetrating peptides: a comparative study, Biochem J., 407(2):285-292.
Santra et al., 2005, Rapid and effective labeling of brain tissue using TAT-conjugated CdS:Mn/ZnS quantum dots, Chem Comm, 3144-3146.

(Continued)

*Primary Examiner* — Julie Ha
(74) *Attorney, Agent, or Firm* — Riverside Law LLP

(57) ABSTRACT

A novel cell penetrating peptide that transports proteins into cells and/or into nuclei and a pharmaceutical containing the peptide is described.

8 Claims, 43 Drawing Sheets

Specification includes a Sequence Listing.

(56) References Cited

OTHER PUBLICATIONS

Eichelbaum et al., 1996, Influence of Pharmacogenetics on Drug Disposition and Response, Clin. Exp. Pharmacol. Physiol., 23:983-985.
Linder et al., 1997, Pharmacogenetics: a laboratory tool for optimizing therapeutic efficiency, Clin. Chem., 43:254-266.
Vaickus, L., 1991, Immune markers in hematologic malignancies, Crit. Rev. Oncol. Hemotol., 11:267-97.
Li, Y. et al., 1999, Design, Synthesis, and Spectroscopic Properties of Peptide-Bridged Fluorescence Energy-Transfer Cassettes, Bioconjugate Chemistry, 10:241-245.
Suwal, S. et al., 2010, Phosphorylation-Dependent Kinase—Substrate Cross-Linking, Angewandte Chemie, 49 (9):1627-1630.
Anjomshoa et al., 2009, Generation of Motor Neurons by Coculture of Retinoic Acid-Pretreated Embryonic Stem Cells with Chicken Notochords, Stem Cells and Development, 18:259-267.
Coyle et al., 2011, Regional Differentiation of Retinoic Acid-Induced Human Pluripotent Embryonic Carcinoma Stem Cell Neurons, PloS one, 6(1):e1674.
Elizalde et al., 2011, Distinct Roles for Wnt-4 and Wnt-11 During Retinoic Acid-Induced Neuronal Differentiation, Stem Cells, 29:141-153.
Engberg et al., 2010, Retinoic Acid Synthesis Promotes Development of Neural Progenitors from Mouse Embryonic Stem Cells by Suppressing Endogenous, Wnt-Dependent Nodal Signaling, Stem Cells, 28:1498-1509.
Donato et al., 2007, Differential development of neuronal physiological responsiveness in two human neural stem cell lines, BMC neuroscience, 8:36.
Benjaminsen et al., 2013, The Possible "Proton Sponge" Effect of Polyethylenimine (PEI) Does Not Include Change in Lysosomal pH, Molecular Therapy, 21(1):149-157.
Marrache et al., 2012, Engineering of blended nanoparticle platform for delivery of mitochondria-acting therapeutics, Proceedings of the National Academy of Sciences, 109(40):16288-16293.
Strehl et al., 2011, Origin and Functional Activity of the Membrane-Bound Glucocorticoid Receptor, Arthritis and Rheumatism, 63:3779-3788.
Kosugi et al., 2011, MUC1-C Oncoprotein Regulates Glycolysis and Pyruvate Kinase m2 Activity in Cancer Cells, PLoS One, 6(11):e28234.
Shvartsburg et al., 2001, Prediction of Peptide Ion Mobilities via a priori Calculations from Intrinsic Size Parameters of Amino Acid Residues, J. Am. Soc. Mass Spectrom. 12:885-888.
Watkins et al., 2009, Cellular uptake, distribution and cytotoxicity of the hydrophobic cell penetrating peptide sequence PFVYLI linked to the proapoptotic domain peptide PAD, Journal of Controlled Release, 140:237-244.
Cho et al., 1993, An unnatural biopolymer, Science, 261:1303-1305.
Akita et al., 2002, Neuronal differentiation of adult rat hippocampus-derived neural stem cells transplanted into embryonic rat explanted retinas with retinoic acid pretreatment, Brain Research, 954(2):286-293.
Lange et al., 2011, Small molecule GSK-3 inhibitors increase neurogenesis of human neural progenitor cells, Neuroscience letters, 488(1):36-40.

* cited by examiner

Figure 14

SEQ ID NO: 8: AAAAAEK-AAAAAEK-AAAAEK-A

Component Analysis
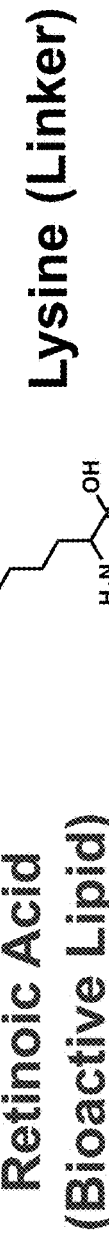
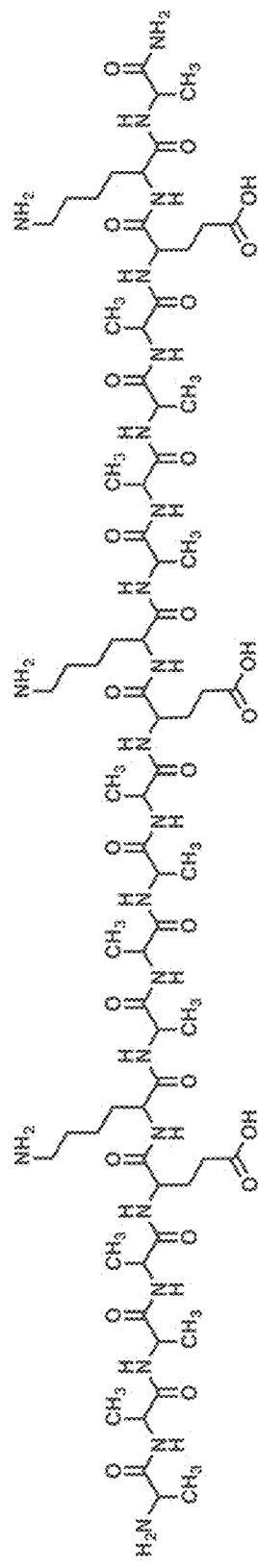
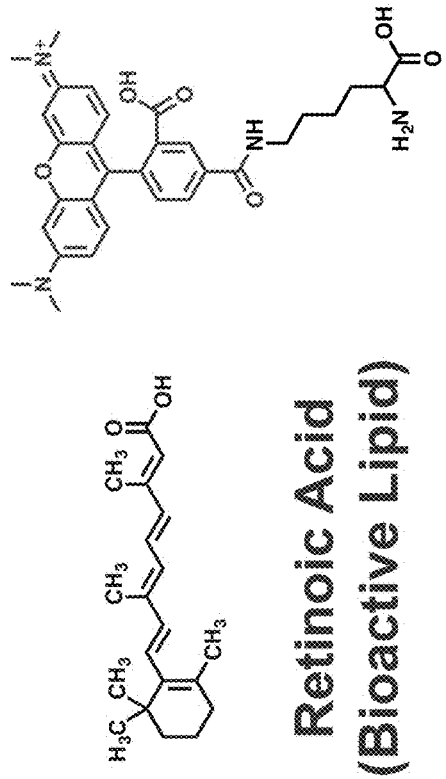
Carboxytetramethylrhodamine (TAMRA)
(Fluorophore or Drug Molecules)
Lysine (Linker)
Retinoic Acid (Bioactive Lipid)
Cell Penetrating Peptide (CPP) PepB
SEQ ID NO: 8: AAAAEK-AAAAEK-AAAAEK-A
Figure 30D

Component Analysis
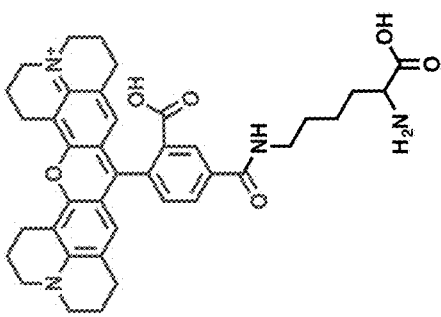
ROX (Fluorophore or Drug Molecules)
Lysine (Linker)
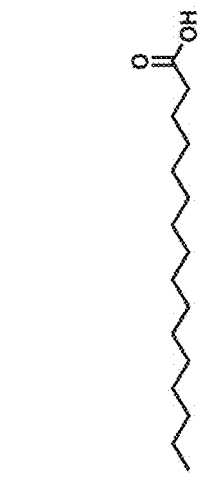
Palmitic Acid (Bioactive Lipid)
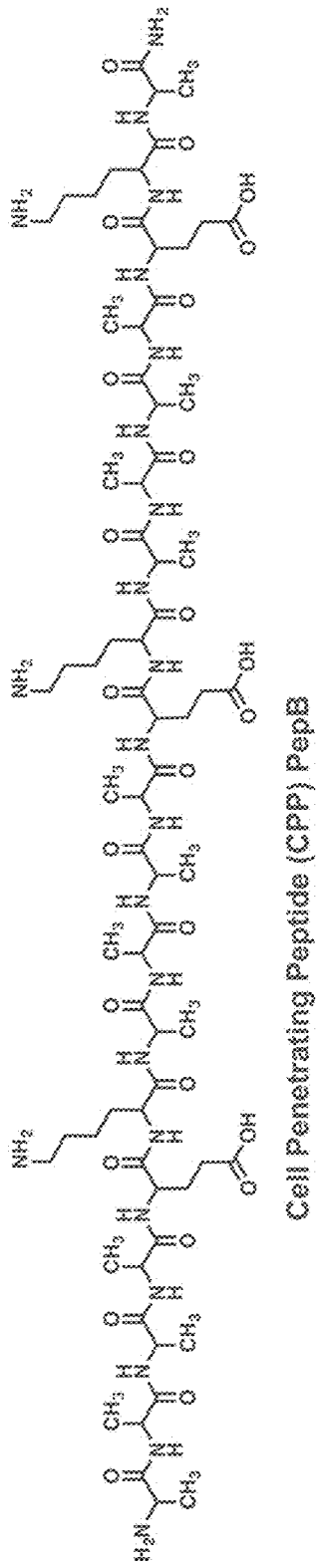
Cell Penetrating Peptide (CPP) PepB
SEQ ID NO: 8: AAAAEK-AAAAEK-AAAAEK-A
Figure 30F

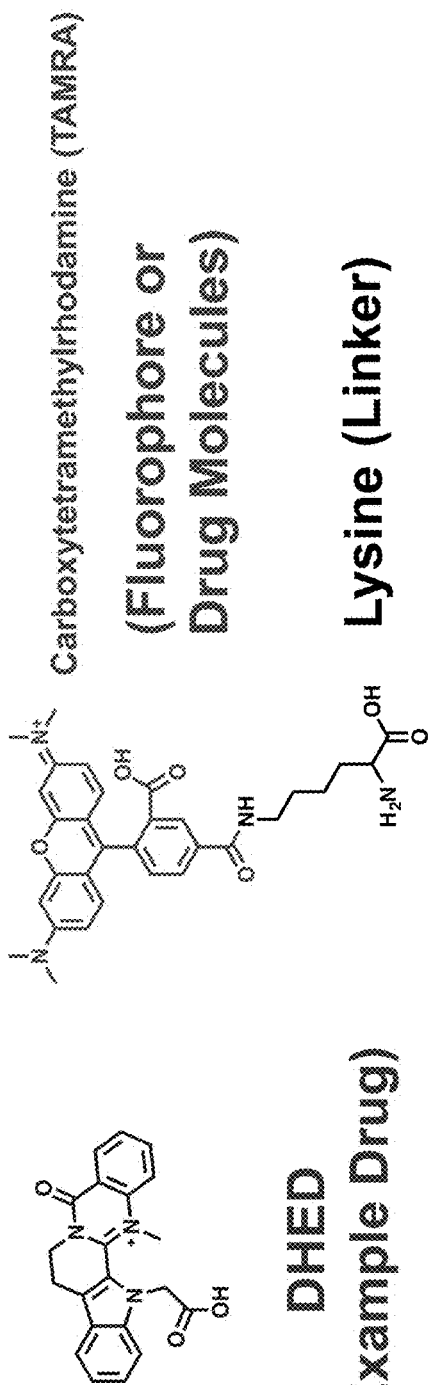
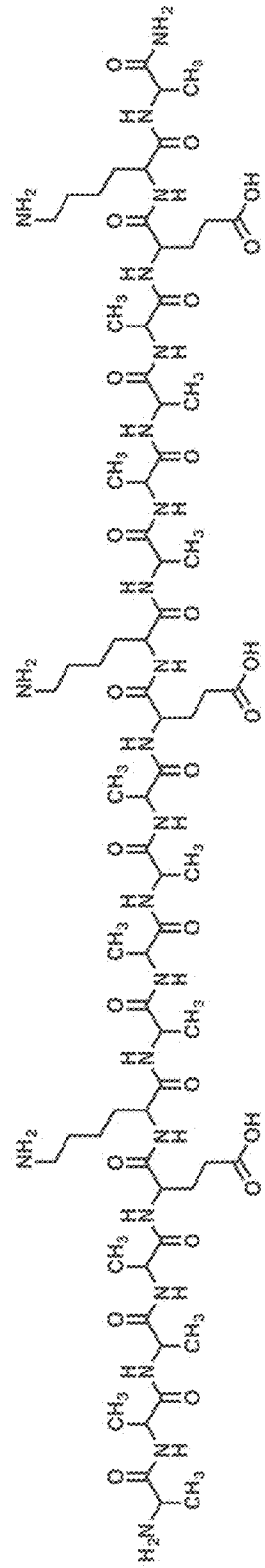
SEQ ID NO: 8: AAAAEK-AAAAEK-AAAAEK-A
Figure 31B

SEQ ID NO: 3

[X]*ATG*GCTGCTGCTGCTGAAAAAGCCGCGCCGAGAAGGCAGCAGCGGGAAAAG
GCG*GGTGGGGAGGGGTGGC*GTGAGCAAGGGCGAGGAGCTGTTCACCGGGGTGGTGC
CCATCCTGGTCGAGCTGGACGGCGACGTAAACGGCCACAAGTTCAGCGTGTCCGGCGAGGGC
GAGGGCGATGCCACCTACGGCAAGCTGACCCTGAAGTTCATCTGCACCACCGGCAAGCTGCCC
GTGCCCTGGCCCACCCTCGTGACCACCCTGACCTACGGCGTGCAGTGCTTCAGCCGCTACCCCG
ACCACATGAAGCAGCACGACTTCTTCAAGTCCGCCATGCCCGAAGGCTACGTCCAGGAGGCA
CCATCTTCTTCAAGGACGACGGCAACTACAAGACCCGCGCCGAGGTGAAGTTCGAGGGCGAC
ACCCTGGTGAACCGCATCGAGCTGAAGGGCATCGACTTCAAGGAGGACGGCAACATCCTGGGG
GCACAAGCTGGAGTACAACTACAACAGCCACAACGTCTATATCATGGCCGACAAGCAGAAGAA
CGGCATCAAGGTGAACTTCAAGATCCGCCACAACATCGAGGACGGCAGCGTGCAGCTCGCCGA
CCACTACCAGCAGAACACCCCCATCGGCGACGGCCCCGTGCTGCTGCCCGACAACCACTACCTG
AGCACCCAGTCCGCCCTGAGCAAAGACCCCAACGAGAAGCGCGATCACACTGGTCCTGCTGGA
GTTCGTGACCGCCGCCGGGATCACTCTCGGCATGGACGAGCTGTACAAGTAA*[Y]

Figure 32A

Start Codon: ATG

SEQ ID NO: 4:
PepB: GCTGCTGCTGCTGAAAAGCCGCCGCCGAGAAGGCAGCAGCGGCGGAAAAGGCG.

SEQ ID NO: 5:
Linker: <u>GGTGGGCGGAGGGGGTGGC</u>

SEQ ID NO: 6:
EGFP (A model Protein):
GTGAGCAAGGGCGAGGAGCTGTTCACCGGGGTGGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTGAAGTTCATCTGCACCACCGGCAAGCTGCCCGTG
CCCTGGCCCACCCTCGTGACCACCCTGACCTACGGCGTGCAGTGCTTCAGCCGCTACCCCGACCACATGAAGCAGCACGACTTCT
TCAAGTCCGCCATGCCCGAAGGCTACGTCCAGGAGCGCACCATCTTCTTCAAGGACGACGGCAACTACAAGACCCGCGCCGAGG
TGAAGTTCGAGGGCGACACCCTGGTGAACCGCATCGAGCTGAAGGGCATCGACTTCAAGGAGGACGGCAACATCCTGGGGCAC
AAGCTGGAGTACAACTACAACAGCCACAACGTCTATATCATGGCCGACAAGCAGAAGAACGGCATCAAGGTGAACTTCAAGATC
CGCCACAACATCGAGGACGGCAGCGTGCAGCTCGCCGACCACTACCAGCAGAACACCCCCATCGGCGACGGCCCCGTGCTGCT
GCCCGACAACCACTACCTGAGCACCCAGTCCGCCCTGAGCAAAGACCCCAACGAGAAGCGCGATCACATGGTCCTGCTGGAGTT
CGTGACCGCCGCCGGGATCACTCTCGGCATGGACGAGCTGTACAAGTAA

Figure 32B

SEQ ID NO: 7:

MAAAAEKAAAAEKAAAAEKAAAAEKAGGGGGVSKGEELFTGVVPILVELDGDVNGHKFSVSGEGE
GDATYGKLTLKFICTTGKLPVPWPTLVTTLTYGVQCFSRYPDHMKQHDFFKSAMPEGYVQERT
IFFKDDGNYKTRAEVKFEGDTLVNRIELKGIDFKEDGNILGHKLEYNYNSHNVYIMADKQKNGI
KVNFKIRHNIEDGSVQLADHYQQNTPIGDGPVLLPDNHYLSTQSALSKDPNEKRDHMVLLEFV
TAAGITLGMDELYK

Figure 33A

M: Initial methionine sequence (Start codon converted)

SEQ ID NO: 8:
AAAAEKAAAAEKAAAAEKA: Model PepB sequence (19-mer).

SEQ ID NO: 9:
GGGGGG: Linker sequence.

SEQ ID NO: 10:
EGFP Protein:
VSKGEELFTGVVPILVELDGDVNGHKFSVSGEGEGDATYGKLTLKFICTTGKLPVPWPTLVTTL
TYGVQCFSRYPDHMKQHDFFKSAMPEGYVQERTIFFKDDGNYKTRAEVKFEGDTLVNRIELK
GIDFKEDGNILGHKLEYNYNSHNVYIMADKQKNGIKVNFKIRHNIEDGSVQLADHYQQNTPIGD
GPVLLPDNHYLSTQSALSKDPNEKRDHMVLLEFVTAAGITLGMDELYK

Figure 33B

SYNTHESIS OF CELL PENETRATING PEPTIDES FOR DRUG DELIVERY AND STEM CELL APPLICATIONS

CROSS-REFERENCE TO RELATED APPLICATIONS

This application is the U.S. national phase application filed under 35 U.S.C. § 371 claiming benefit to International Patent Application No. PCT/US15/53722, filed Oct. 2, 2015, which is entitled to priority under 35 U.S.C. § 119(e) to U.S. Provisional Patent Application No. 62/058,796, filed Oct. 2, 2014, each of which application is hereby incorporated herein by reference in their entireties.

BACKGROUND OF THE INVENTION

Cell penetrating peptides (CPPs) actively transport into mammalian cells across the plasma membrane barrier. CPPs are commonly derived from proteins such as the HIV-1 transcriptional activator (TAT) (Torchilin et al., 2001 Proc. Natl. Acad. Sci. 98: 8786-8791), the Antennapedia homeodomain (Antp) (Zhang et al., 2005 Biochemistry 44: 10110-10118), and the murine vascular endothelial cadherin (pVEC) (Nan et al., 2011 J. Pept. Sci. 17: 812-817). The lengths of CPPs typically range from 30-50 amino acids and such lengths can lead to preparative challenges since solid phase peptide synthesis (SPPS) methods are (commonly) utilized for their preparation (Suh et al., 2001 Comprehen. Biomat. 4: 219-245; Suh et al., 2013 Polymer Adhesion, Friction and Lubrication, 283-317 (Wiley)).

Although these CPPs have been proven to be potentially suitable for the delivery of peptides, proteins, oligonucleotides, nano-particles and any bioactive molecule into cells, they all suffer from limitations, such as their effectiveness being restricted to a subset of cargo molecules. Other peptides are relatively inefficient in the delivery of cargo molecules or have at least some specificity for delivery to various tissues (Mueller et al., Bioconjugate Chem., 2008, 19 (12), pp 2363-2374; El-Andaloussi et al., Biochem J. 2007 Oct. 15; 407(Pt 2): 285-292).

Thus, there is a need in the art to develop additional, superior CPPs. The present invention satisfies this unmet need.

SUMMARY OF THE INVENTION

The invention provides a composition comprising a cell penetrating peptide (CPP), wherein the CPP comprises the sequence of AAAAEK (SEQ ID NO: 1) or a variant thereof.

In one embodiment, the CPP comprises from about 5 to about 20 consecutive amino acid residues comprising the sequence of AAAAEK (SEQ ID NO: 1) or a variant thereof.

In one embodiment, the CPP comprises a repeated sequence of SEQ ID NO: 1.

In one embodiment, the CPP comprises a terminal alanine after the sequence of SEQ ID NO: 1.

In one embodiment, the CPP is linked to a cargo.

In one embodiment, the cargo is conjugated to the peptide at the N-terminus of the peptide.

In one embodiment, the cargo is conjugated to the peptide at the C-terminus of the peptide.

In one embodiment, the cargo molecule is selected from the group comprising a nucleic acid molecule, an amino acid molecule, a therapeutically active peptide, a protein, a carbohydrate, a lipid, a contrast or imaging agent, a quantum dot, a diagnostic agent, a therapeutic agent, and any combination thereof.

In one embodiment, the cargo is selected from the group consisting of a single strand oligonucleotide, a double-strand oligonucleotide, a plasmid, a synthetic nucleotide analogue, and any combinations thereof.

In one embodiment, the cargo is selected from the group consisting of a cell homing peptide, an aptamer, a receptor ligand, a spacer comprising a cleavable site coupled to an inactivating peptide, a peptide ligand, a cytotoxic peptide, a bioactive peptide, an antibody, a protein, and any combination thereof.

The invention provides a method of delivering a cargo into a cell, the method comprising contacting a cell with the composition of the invention thereby delivering a cargo into the cell.

In one embodiment, the cell is a stem cell.

The invention provides a method of treating, preventing or ameliorating a disease in a patient in need of such treatment, prevention or amelioration, the method comprising administering the composition of the invention to the patient thereby treating, preventing or ameliorating the disease.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 8, comprising

FIGS. 12A through 12D, is a series of images depicting quantitative real-time PCR (qRT-PCR) analysis of neural stem cell (Nestin, SOX2), early neuron (Tubb3), mature neuron (MAP2), and astrocyte (GFAP)-specific gene expression in ReNcell VM after (FIG. 12A) 1 week, (FIG. 12B) 2 week, (FIG. 12C) 3 week, and (FIG. 12D) 4 weeks of differentiation in the presence of the chemicals including RA, RA-PepB (PepB is also referred herein as PepX), C16-PepB, LiCl and IFNγ. GAPDH served as control.

FIGS. 13A through 13D, is a series of images depicting quantitative real-time PCR (qRT-PCR) analysis of early neuron (Tubb3) and mature neuron (MAP2)-specific gene expression in ReNcell VM after (FIG. 13A) 1 week, (FIG. 13B) 2 week, (FIG. 13C) 3 week, and (FIG. 13D) 4 weeks of differentiation in the presence of the chemicals including RA, RA-PepB, C16-PepB, LiCl and IFNγ. The statistical significance was evaluated compared to the control (differentiated ReNcell VM without chemicals) *P<0.05, **P<0.01. GAPDH served as control.

FIG. 14. Mitochondria-stained ReNcell VM. After treatment of RA-PepB for 4 weeks, cells were differentiated and stained with Mito-GFP BacMam (60× magnification).

(FIG. 19A) Neurospheres inside the gel, (FIG. 19B) image taken at different location and Z-height compatible to A, and (FIG. 19C) 3D reconstruction image of a neurosphere stained with calcein AM. The green fluorescence (from calcein molecules) in the images show that the cells are living at the time of the staining process.

FIGS. 30A-30G depict synthetic PepB constructs. FIG. 30A depicts RA-PepB Labeled with the ROX Dye. FIG. 30B depicts the component analysis of RA-PepB Labeled with the ROX Dye. FIG. 30C depicts RA-PepB Labeled with the TAMRA Dye. FIG. 30D depicts component analysis of RA-PepB Labeled with the TAMRA Dye. FIG. 30E depicts C16-PepB Labeled with the ROX Dye. FIG. 30F depicts component analysis of C16-PepB Labeled with the ROX Dye. FIG. 30G depicts C16-PepB Labeled with the TAMRA Dye.

FIG. 31B depicts the component analysis of DHED(TAMRA)PepB.

FIG. 32A shows the entire DNA sequence of a representative DNA vector system (SEQ ID NO: 3). Restriction enzyme cleavable sequences are designed as: [X] and [Y] (these will depend on the vector utilized). Insertion points: *. Additional sites to include nucleic acid codes depending on the vector map and specific need.

FIG. 32B shows a component analysis of the DNA vector system of FIG. 32A. PepB is SEQ ID NO: 4; Linker is SEQ ID NO: 5; EGFP is SEQ ID NO: 6.

FIG. 33A the sequence of a fusion protein (i.e., PepB-Gly6-EGFP) incorporating the PepB sequence on the N-terminus (SEQ ID NO: 7).

FIG. 33B shows a component analysis of the fusion protein. The model PepB sequence is SEQ ID NO: 8; Linker sequence is SEQ ID NO: 9; EGFP is SEQ ID NO: 10.

DETAILED DESCRIPTION

Figure 1:
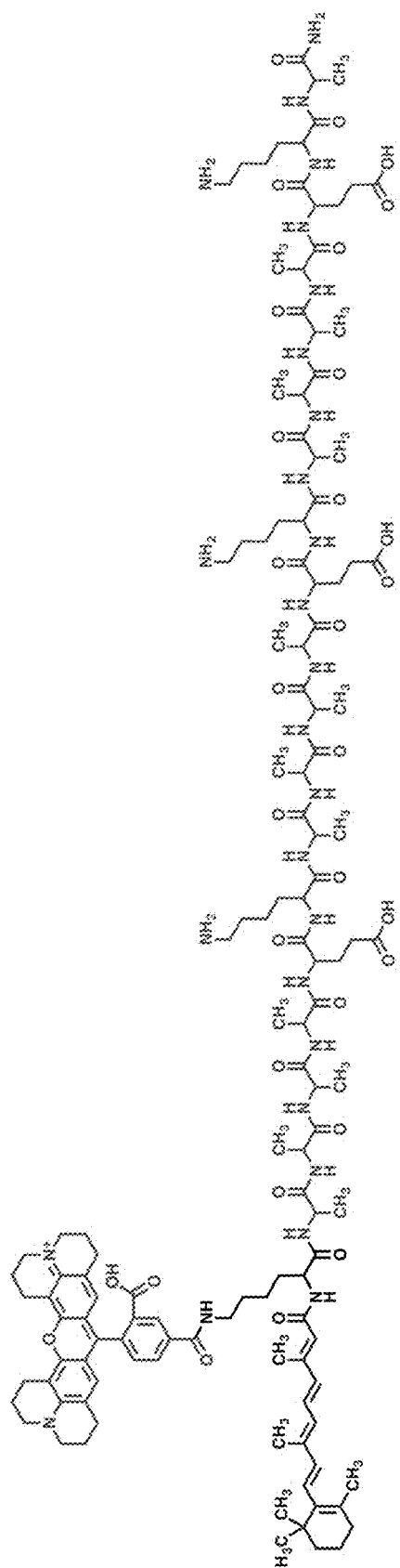
FIG. 1 is a schematic of the chemical Structure of RA-ROX-AKEA (RA-ROX-$(A_4EK)_3A$). As referred elsewhere herein, RA-ROX-AKEA=RA-ROX-PepB.

The invention is based on the discovery of a short CPP that exhibits cell penetrating activity not only in soluble conditions but also in gel-like conditions. In one embodiment, the CPP of the invention is a peptide comprising AAAAEK (SEQ ID NO. 1). In some instances, the CPP comprises at least a repeat of SEQ ID NO. 1. In some instances, the sequence of SEQ ID NO. 1 is repeated at least three times. In some instances, the CPP of the invention comprises an alanine after the AAAAEK sequence. In some instances, the CPP of the invention comprises an alanine after the repeated AAAAEK sequences.

The CPP of the invention can be conjugated to any molecule of interest to increase cellular uptake when combined with the desired molecule. That is, the CPPs of the invention can act as carrier moieties to facilitate movement of a cargo across cell and nuclear membranes. Accordingly, peptide-cargo conjugates are also included in the invention.

The CPP of the invention can also be used as a cellular tagging agent as well as vehicles for (protein) drug delivery and stem cell applications.

In one embodiment, the peptide cargo molecule comprises a peptide having therapeutic activity and in a more preferred embodiment a therapeutic activity to treat a disease.

In one embodiment, the cargo molecule comprises a pharmaceutically active compound.

In one embodiment, the present invention provides a composition comprising at least one CPP and optionally at least one separate cargo molecule. According to some embodiments the at least one CPP provides the function of the cargo molecule and so no cargo molecule or other therapeutically active molecule is present; for these embodiments, preferably the composition comprises a pharmaceutically suitable carrier. As used herein, the term "separate" does not necessarily mean that the cargo molecule is not linked, covalently or non-covalently, to the CPP.

In one embodiment, the present invention provides a composition comprising a complex as described elsewhere herein.

In one embodiment, the present invention provides a composition comprising a fusion and/or a conjugate as described elsewhere herein.

In one embodiment, the present invention provides a nucleic acid coding for any one of the CPPs. According to a further embodiment the nucleic acid coding for any one of the CPPs has a nucleic acid sequence encoding a peptide comprising the sequence of SEQ ID NO: 1, or a variant thereof.

In one embodiment, the present invention provides a composition comprising a nucleic acid coding for any one of the CPPs and a cargo molecule.

In one embodiment, the cargo molecule is a nucleic acid preferably with a therapeutic effect, such as antisense molecule, PNA, siRNA molecule or an miRNA molecule.

In one embodiment, the cargo molecule is a nucleic acid coding for a peptide such as for example, therapeutic peptide, ligand, enzyme, recombinant proteins, and the like.

In one embodiment, the nucleic acid coding for the CPP is covalently linked to, or otherwise provided with, the nucleic acid coding for another, therapeutic peptide, such that the CPP and the therapeutic peptide would be co-expressed in the same cell.

In one embodiment, the nucleic acid coding for the CPP and the nucleic acid coding for a peptide are linked in-frame.

In one embodiment, the peptide is a pharmaceutically active agent.

In one embodiment, the present invention provides use of CPP as a transfection agent.

In one embodiment, the present invention provides use of a composition according to at least some embodiments of the present invention for the manufacture of a medicament.

In one embodiment, the cargo molecule is a pharmaceutically active agent.

In one embodiment, the present invention provides use of a composition according to at least some embodiments of the present invention for the manufacture of a diagnostic agent.

In one embodiment, the cargo molecule is a drug or disease related marker, such as diagnostic marker to diagnose an existing disease, and/or a prognostic marker to detect if such a disease may develop. Preferably, such markers can enable the detection of the levels and activities of specific targets and more preferably, such markers can enable the detection of the levels and activities of specific intracellular targets.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "amino acid sequence variant" refers to polypeptides having amino acid sequences that differ to some extent from a native sequence polypeptide. Ordinarily, amino acid sequence variants will possess at least about 70% homology, or at least about 80%, or at least about 90% homology to the native polypeptide. The amino acid sequence variants possess substitutions, deletions, and/or insertions at certain positions within the amino acid sequence of the native amino acid sequence.

As used herein, the term "binding" refers to the adherence of molecules to one another, such as, but not limited to, enzymes to substrates, antibodies to antigens, DNA strands to their complementary strands. Binding occurs because the shape and chemical nature of parts of the molecule surfaces are complementary.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

As used herein, the term "attachment" or "attaching" refers to conjugation, fusion, complexation or association between at least two molecular entities (e.g. CPP and a cargo) which may be referred to as a single entity.

A "cell penetrating domain" is used herein to refer to a domain that facilitates the entry of said domain, along with any molecule associated with the domain, across one or more membranes to the interior of a cell.

A "cell penetrating peptide" is used herein to refer to a polypeptide that facilitates the entry of said polypeptide, along with any molecule associated with the polypeptide, across one or more membranes to the interior of a cell.

As used herein, the term "cargo" or "cargo molecule" refers to an entity which is transported or more efficiently delivered inside the cell using any one of the CPPs. The cargo molecule optionally includes, but is not limited to, one or more of any one of nucleic acids, oligonucleotides such as siRNA, dsRNA, miRNA, DNA, RNA, PNA, antisense molecules, ribozymes, aptamers, spiegelmers, decoy molecules, antibodies, amino acids, peptides, proteins, lipids, carbohydrates, small molecules and combinations thereof. The cargo molecule may optionally comprise any type of cellular effector. A cellular effector can be either an intracellular and/or extracellular effector and is in the present context defined as a molecule that produces a cellular effect, such as a contraction, secretion, electrical impulse, or activation or inactivation of an intracellular and/or extracellular signaling cascade, or that induces the up regulation of a cellular level of an mRNA and/or a protein, in response to a stimulation by said effector. A typical effector is in the present context selected from the group consisting of a metabolite, an antagonist, an agonist, a receptor ligand, a receptor coupled protein, an activated receptor, an enzyme inhibitor, activator/inactivator and/or stimulator, a kinase, a phosphatase, an enhancer, or a silencer, a transcription factor, a transporter and/or a transmitter, a hormone, a channel, an ion, a prion, and a viral protein.

As used herein, the terms "conservative variation" or "conservative substitution" as used herein refers to the replacement of an amino acid residue by another, biologically similar residue. Conservative variations or substitutions are not likely to substantially change the shape and/or activity of the peptide chain. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein, polypeptide or peptide, refers to a subsequence of a larger protein or peptide. A "fragment" of a protein, polypeptide, or peptide can be at least about 5 amino acids in length; for example, at least about 10 amino acids in length; at least about 20 amino acids in length; at least about 50 amino acids in length; at least about 100 amino acids in length; at least about 200 amino acids in length; or at least about 300 amino acids in length (and any integer value in between).

As used herein, the term "fusion peptide" or "fusion polypeptide" or "fusion protein" or "fusion peptidomimetic" refers to a heterologous peptide, heterologous polypeptide, heterologous protein, or peptidomimetic linked to a CPP.

The terms "fusion" or "conjugate" as used herein, refer to a CPP or CPPs that are bond (e.g. a peptide bond, disulfide bond) to at least one type of cargo molecule.

As used herein, the term "homologous proteins" or "homologs" refers to proteins that look similar by way of amino acid sequences and can work in similar ways in different species of organism. When the sequences are aligned, homologous proteins have exactly the same amino acid residues at certain amino acid positions in the polypeptide (i.e., highly conserved regions) and also similar amino acid residues at other amino acid positions in the polypeptide.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

As used herein, the term "linkage group" refers to any molecular entity, such as polymer, peptide, hydrophobic or polar peptide, protein, lipid, dendrimers, etc., which links two molecular entities preferably by a covalent bond.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "treatment" or "treating" encompasses prophylaxis and/or therapy. Accordingly the compositions and methods of the present invention are not limited to therapeutic applications and can be used in prophylaxis ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition, i.e., arresting or reducing the development of the disease or at least one clinical or subclinical symptom thereof, or (iii) relieving the disease, i.e. causing regression of the state, disorder or condition or at least one of its clinical or subclinical symptoms.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition associated with ocular angiogenesis, including alleviating symptoms of such diseases.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to peptides particularly, although not exclusively, to cell penetrating peptides and to conjugates of a cell penetrating peptide and a cargo molecule.

Accordingly, the present invention provides peptides that are useful in facilitating the uptake of such cargoes across cell membranes, such as the plasma membrane of a mammalian cell and/or the nuclear membrane of a mammalian cell.

The peptides may be referred to as "cell penetrating peptides" and may be conjugated to a cargo to facilitate transport of the cargo across the membrane.

The peptides and peptide-cargo conjugates according to the present invention can be provided for use in a method of medical treatment. The medical treatment may preferably require delivery of the cargo molecule into a cell and optionally the nucleus of the cell.

The peptides and peptide-cargo conjugates according to the present invention can be provided for use in a method of experimental research. The research may preferably require delivery of the cargo molecule into a cell and optionally the nucleus of the cell. In some instances, the cell is a stem cell.

Composition

In one embodiment, the invention provides a CPP having an amino acid sequence of AAAAEK (SEQ ID No. 1) or a homolog, fragment or a derivative thereof. In another embodiment, the CPP comprises repeated sequence of AAAAEK. In another embodiment, the CPP comprises an alanine following the repeated sequence of AAAAEK. However, the invention should not be limited to a terminal alanine. Rather, any suitable spacer can be used so long as the peptide maintains CPP activity.

Excluding the cargo molecule, in one embodiment, CPPs according to the present invention may have a length of less than 10 amino acids, more preferably one of 4, 5, 6, 7, 8, 9, amino acids. In some instances, the peptide sequence can be repeated twice, three times, four times, five times, or more.

Excluding the cargo molecule, in one embodiment, CPPs according to the present invention may have a maximum length of 30 amino acids, more preferably one of 15, 16, 17, 18, 19, 20, 21, 22, 23, 24, 25, 26, 27, 28, 29, 30 amino acids and a minimum length of 10 amino acids, more preferably one of 10, 11, 12, 13, 14, 15, 16, 17, 18, 19, 20 amino acids (the maximum and minimum length optionally excludes any spacer molecules, e.g. aminohexanoyl groups, but includes non-natural or modified amino acids).

Peptides according to the present invention may be provided as peptide-cargo conjugates where the peptide further comprises a cargo molecule chemically linked (preferably covalently linked) to the peptide at either the N-terminal or C-terminal end of the peptide. Chemical linkage may be via a disulphide bond, thioether, thiol-maleimide linkage or the like.

The cargo molecule may be any small molecule, e.g. small molecule drug, peptide, cyclic peptide, protein, pharmaceutical or therapeutic (e.g. molecular weight less than 5,000 Da, preferably less than 3000 Da or less than 1000 Da). The cargo molecule may be a nucleic acid, antisense oligonucleotide (such as PNA, PMO, LNA), or siRNA.

In one embodiment, a cell-penetrating peptide, also referred herein as a "peptide carrier", is a molecule, the core of which is a peptide. Other chemical groups can however be covalently bound to the peptidic core, in order to improve the overall stability of the molecule, and/or to provide it with additional properties, such as targeting ability. For example, a cell-penetrating peptide according to the invention can further comprise, covalently linked to the C-terminal extremity of the peptidic core of SEQ ID No: 1, one or several groups chosen amongst a cysteamide, a cysteine, a thiol, an amide, a carboxyl, a linear or ramified $C_1$-$C_6$ alkyl optionally substituted, a primary or secondary amine, an osidic derivative, a lipid, a phospholipid, a fatty acid, a cholesterol, a poly-ethylene glycol, a nuclear localization signal (NLS), and/or a targeting molecule. Alternatively or additionally, the cell-penetrating peptide of the invention can also comprise, covalently linked to the N-terminal end of the peptidic core of SEQ ID No: 1, one or several chemical entities chosen amongst an acetyl, a fatty acid, a cholesterol, a poly-ethylene glycol, a nuclear localization signal, and/or a targeting molecule. If necessary, for example in the case of N-terminal addition of cholesterol, a peptidic bridge can be used to bind a non-peptidic molecule to the peptidic core of the CPP.

According to at least some embodiments but without wishing to provide a closed list, the present invention provides complexes, fusions and/or conjugates of the CPPs, wherein the peptide is preferably attached to another entity through any one of the following: 1) Conjugation chemistry (optionally through derivatization of one or both of the peptide and/or the cargo) and hence formation of a covalent bond: a) conjugates through Carboxyl groups, b) conjugates through free amines, c) conjugates through the thiol group on cysteine, d) conjugates through one or more added moieties for derivatization of one or both of the peptide and/or the cargo, including optionally through any of the groups of a-c; 2) Non covalent interactions between the CPP and another entity/ies, and hence formation of a non-covalent bond: a) complexation-solution of CPP(s) and molecular entity in different proportions, b) complexation as (a) with additional carrier proteins such as Keyhole limpet hemocyanin (KLH), bovine serum albumin (BSA), ovalbumin (OVA) or Rabbit Serum Albumin (RSA).

With regard to the above non-covalent bond, optionally such a non-covalent bond may comprise one or more of ionic bonds, hydrogen bonds or hydrophobic interaction or a combination of such bonds.

According to at least some embodiments of the present invention, such a covalent bond may optionally be formed through any chemical groups, polymers, peptides, proteins or other linkers known in the art. Such linkers may be chosen to be composed of flexible residues like Glycine and Serine so that the adjacent entities (e.g. CPP and cargo) are free to move relative to one another or such that the inherent biological or therapeutic function of the cargo and CPP must remain or improved or at least should not be worsen after modification and conjugation (as the flexible linker Gly-Gly described in Watkins, et al., Journal of Controlled Release 2009, 140:237-244, to conjugate between the pro-apoptotic peptide and a CPP or as Valine-citruline (Val-Cit) pairs which may be linked to cargos from the family of drugs such as monomethyl auristatin E (MMAE)). Alternatively, such linkers may be chosen to be selective cleavable (e.g. by enzyme-cleavable) as disulfide-based linkers.

According to further embodiments, the peptide further comprises a moiety which is suitable for any detection scheme or tracing methodology for in vivo or in vitro constellation, using a fluorescent reading instrument including but not limited to fluorescence microscope, flow cytometer or magnetic resonance imaging (MRI) device, whereby such moiety is preferably biologically non-reactive and selected from the group comprising fluorophores, radioactive tracers, magnetic labeling, haptens and biotin such that the latter for example, in its simplest form, avidin-biotin detection methods entail applying a biotinylated probe to a sample and then detecting the bound probe with a labeled avidin or streptavidin.

According to further embodiments, the CPP is radioactively labeled, preferably by having incorporated a radioactively labeled amino acid.

According to at least some embodiments the present invention provides a complex, a fusion, and/or a conjugate, comprising a peptide selected from the CPPs attached to a cargo molecule.

According to further embodiments the cargo molecule is covalently or non-covalently attached to the CPP.

In one embodiment, the cargo molecule is selected from the group consisting of nucleic acids, amino acids, peptides, proteins, carbohydrates, lipids, and small molecules and mixtures of any of thereof.

In one embodiment, the cargo molecule is present in a structure or part of a structure, whereby the structure is selected from the group comprising nanoparticles, microparticles, liposomes, carbon nano-tubes and micelles.

In one embodiment, the nucleic acid cargo molecule comprises a nucleic acid selected from the group comprising DNA molecules, RNA molecules, PNA molecules, siRNA molecules, miRNA molecules, antisense molecules, ribozymes, aptamers, spiegelmers and decoy molecules.

In one embodiment, the peptides according to the invention have a sequence that is a chemically contiguous single molecule. The peptide sequence may be comprised of amino acids and optional non-amino acids, e.g. aminohexanoyl spacers. For example, in some parts of the peptide an aminohexanoyl spacer may be chemically bonded to the C-terminal end of a first amino acid and to the N-terminal end of a second amino acid, thereby chemically linking the two amino acids.

The peptides may also include modified and non-naturally occurring amino acids.

Peptides according to the present invention may be provided in isolated or purified form, with or without a cargo molecule.

The invention also provides a variant peptide, which may comprise 1, 2, 3, 4, 5 or more amino acid substitutions from the sequence AAAAEK or repeats of AAAAEK. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid.

Derivatives of the peptides also form part of the present invention. Peptide derivatives include variants of a given peptide sequence (e.g. SEQ ID NO: 1) which have substantial amino acid sequence identity (e.g. 90%, 91%, 92%, 93%, 94%, 95%, 96%, 97%, 98%, 99% or 100%) to the full length peptide and preferably have the same cell penetrating activity. Peptide derivatives may have 1, 2 or 3 amino acids or spacer molecules more or less than SEQ ID NO: 1.

Percentage (%) sequence identity is defined as the percentage of amino acid residues (optionally including spacer groups) in a candidate sequence that are identical with residues in the given listed sequence (referred to by the SEQ ID NO.) after aligning the sequences and introducing gaps if necessary, to achieve the maximum sequence identity, and not considering any conservative substitutions as part of the sequence identity. Sequence identity is preferably calculated over the entire length of the respective sequences.

Alignment for purposes of determining percent amino acid sequence identity can be achieved in various ways known to a person of skill in the art, for instance, using publicly available computer software such as ClustalW 1.82.

T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

Peptide derivatives may also comprise conservative amino acid replacements which, for example, may be between amino acids within the following groups: (i) glycine, alanine, serine, threonine; (ii) glutamic acid and aspartic acid; (iii) arginine, histidine and lysine; (iv) asparagine and glutamine; (v) isoleucine, leucine and valine; (vi) phenylalanine, tyrosine and tryptophan.

If necessary, several well-known chemical strategies can be used by one skilled in the art for transforming a CPP into a drug candidate with increased stability in vivo, bioavailability and/or biological activity; such as: N- and C-terminus modifications to prevent exopeptidase degradation, C-terminal amidation, N-terminal acetylation increases peptide lipophiliocity, cyclization by forming a disulfide bridge, alkylation of amide nitrogen to prevent endopeptidase degradation, introduction of non-natural amino acids to modify the recognition site of the endopeptidase (2-methylalanine, alpha-dialkylated glycine, oligocarbamate, oligourea, guanidino or amidino backbones), incorporation of non-genetically encoded amino acids (methylation, halogenation or chlorination of glycine or phenylalanine) into the CPP amino acid sequence, replacement of some or even all the L-amino acids with their corresponding D-amino acid or beta-amino acid analogues. Such peptides may be synthesized as "inverso" or "retro-inverso" forms, that is, by replacing L-amino acids of the sequence with D-amino acids, or by reversing the sequence of the amino acids and replacing the L-amino acids with D-amino acids. Structurally, the retro-inverse peptide is much more similar to the original peptide than the simple D-analogue. D-peptides are substantially more resistant to peptidases, and therefore are more stable in serum and tissues compared to their L-peptide counterparts. In a preferred embodiment CPPs containing L-amino acids are capped with a single D-amino acid to inhibit exopeptidase destruction, synthesis of CPP-derived oligocarbamate; the oligocarbamate backbone consists of a chiral ethylene backbone linked through relatively rigid carbamate groups (Cho et al., Science 261:1303-1305 (1993)).

In another embodiment, the CPP contains contiguous or non-contiguous basic amino acid or amino acid analog, particularly guanidyl or amidinyl moieties. The terms "guanidyl" and "guanidine" are used interchangeably to refer to a moiety having the formula —HN=C(NH$_2$)NH (unprotonated form). As an example, arginine contains a guanidyl (guanidino) moiety, and is also referred to as 2-amino-5-guanidinovaleric acid or α-amino-δ-guanidinovaleric acid. The terms "amidinyl" and "amidino" are used interchangeably and refer to a moiety having the formula —C(=NH)(NH$_2$). A "basic amino acid or amino acid analog" has a side chain pKa of greater than 10. Preferred highly basic amino acids are histidine, arginine and/or lysine.

Internalization Characterization

The activity of the peptide according to at least some embodiments of the invention as a CPP, or CPP activity, may be determined by conjugation of the respective peptide to a detectable label, for example, fluorophore such as FAM (Carboxyfluorescein) that in this case serves both as a reporter group and as a cargo molecule, and enables the detection and quantification of cellular uptake by methods known to those familiar with the art. Cellular uptake may optionally be determined by quantifying the amount of CPP with cargo, without cargo or only cargo inside the cell, within certain compartments as nucleus, cytoplasm or any other. Such a method should distinguish between intracellular and extracellular compartmentalization (e.g. confusing a non-specific binding of CPP to extracellular membrane as intracellular localization using a subjective detection method will lead to misleading uptake conclusions) and distinguishing between CPP intracellular delivery capability, cargo ability to penetrate the cell and synergistic effect (e.g. in the example described below, a pro apoptotic peptide is delivered into the cell. Intracellular uptake of that peptide using CPPs is assessed by cell viability assay while the pro-apoptotic peptide by itself does not penetrate cellular membrane, thus cells remain viable). Such methods include but are not limited to (i) flow cytometry and fluorescent microscopy for fluorophores serving as reporter group or (ii) fixation and permeabilization of cells followed by incubation with a reagent suitable for the detection by a functional assay as for the previously described cell viability assay, RNA silencing or any other suitable assay. Alternatively, the CPP may be radioactively labeled, e.g. by incorporation of radioactively labeled amino acids and the cellular uptake determined by radiography. The latter method enables the determination of uptake and distribution for the peptides alone, without any cargo. It is understood that to the degree the respective method so permits, the uptake and distribution may also be determined and quantitated for tissues and whole organisms. Alternatively, the uptake may be determined indirectly by means of the biological activity of a cargo molecule attached to the CPP and with the cargo molecule exerting its biological activity only if the molecule enters the cell and reaches a particular subcellular localization such as the cytoplasm or nucleus.

In a further embodiment, the peptides according to at least some embodiments of the present invention optionally comprise a moiety which is suitable for detection. More specifically, such moiety allows for the detection of the peptide. The moiety may be any group suitable for such purpose. Respective moieties are known to the ones skilled in the art and comprise, however, are not limited to, fluorophores, such as for example carboxyfluorescein, or biotin. Preferably the detection occurs by means of fluorescence. Alternatively, the detection may also occur by means of radioactivity, e.g. after incorporation of Iodine by protocols known to those skilled in the art. Detection may occur at the level of an individual cell, a tissue, an organ or an animal. Preferably the animal is a mammal and more preferably selected from the group comprising a dog, a cat, a sheep, a goat, a rat, a mouse, a cow, a horse and a human being.

Cargo Types and Alternatives

In one embodiment the cargo molecule is a nucleic acid, wherein the nucleic acid is any polymer comprising of at least two nucleotides which are covalently linked. In one embodiment a nucleic acid can be a DNA molecule or a RNA molecule or a mixture thereof. It is also within at least some embodiments of the present invention that the nucleic acid consists of L-nucleotides, D-nucleotides or mixtures. In a further embodiment, the base moiety, the sugar moiety and/or the phosphate moiety of the individual nucleotide can be individually and independently modified for each and any of the nucleotides forming the nucleic acid or the respective analog. Particularly, preferred modified sugar moieties are those having a methyl, methoxy, ethyl or ethoxy group at the 2' atom of the sugar moiety. Particularly, preferred modified phosphat moieties are phosphothioates. In another embodiment, peptide nucleic acids are employed.

In another embodiment the cargo molecule is a peptide, comprising of at least two amino acids which are covalently linked, preferably through a peptide bond. In an embodiment the peptide consists of L-amino acids, D-amino acids or mixtures thereof. The amino acids may be any amino acids, whether naturally occurring or non-natural. In a preferred embodiment the term peptide thus also comprises peptides and proteins as generally understood in the art. The peptides or proteins may be purified from natural sources, obtained through organic synthesis or obtained by conjugation of synthetic amino acids or peptides to peptides or proteins obtained from natural sources by protocols familiar to those skilled in the art and exemplified but not limited to native chemical ligation. Preferably, peptides will have a length of 2 to 40 amino acids, more preferably of 2 to 30 amino acids, more preferably of 4 to 25, more preferably of 4 to 20, and more preferably of 4 to 17 amino acids. As used herein, the term protein preferably refers to a polypeptide containing secondary structure and more preferably tertiary structure.

In another embodiment the cargo molecule is a small molecule, whereby a small molecule is preferably a molecule having a molecular weight of 1000 Daltons or less and more preferably representing a drug or a drug candidate. Particularly preferred classes of small molecules are heterocyclic small molecules.

In another embodiment the cargo molecule is a lipid or a substructure of a lipid such as a moiety thereof. Preferably, a molecule of this class will exert a particular function once acting on the cell either inside or in the plasma membrane. An example for the former is diacylglycerol. This example illustrates that a lipid exerting such particular function is preferably selected from the group comprising intracellular messengers. An example for the latter and thus representing a possible cargo molecule is a lipopeptide, preferably a lipopeptide with a S-[2,3-bis(palmitoyloxy)-(2RS)-propyl]-N-palmitoyl-(R)-cysteinyl-(S)-se-ryl-tetra-(S)-lysine moiety and most preferably a peptide with a S-[2,3-bis(palmitoyloxy)-(2RS)-propyl]-N-palmitoyl-(R)-cysteinyl-(S)-sery-1-tetra-(S)-lysine acting as an agonist or antagonist of a Toll-like receptor.

In another embodiment the cargo molecule is a carbohydrate.

In another embodiment the cargo is a contrasting agent used for magnetic resonance imaging. Such contrasting agents are for example but not limited to gadolinium (III)-DTPA (diethylenetriamine-pentaacetic acid) or gadolinium (III)-DOTA (1,4,7,10-Tetraazacyclododecane-1,4,7,10-tetraacetic acid).

In another embodiment, the cargo molecule is a particle. A particle may be a polymer particle, consisting, for example, of cross-linked polystyrene, cross-linked N-(2-hydroxypropyl)methacrylamide, cross-linked dextran, a liposome, or a micelle. Preferably, the particle serves as a carrier or container for a functional molecule. The functional molecule may be any molecules exerting a function inside cells, e.g. chemotherapeutics and oligonucleotides and preferably those that may also serve as cargo molecules for the CPPs according to at least some embodiments of the present invention. In general coupling of the functional molecule to the particle, respectively loading of the functional molecules into the particle, is intended to improve the pharmacokinetic properties of the functional molecule, e.g. by prolonging its circulation in the organism while coupling of the peptide(s) according to at least some embodiments of the present invention mediates the delivery of these functional molecules into cells. In addition to the peptide(s) according to at least some embodiments of the present invention, the particles may further be modified by a moiety or a molecule that mediate a targeting of the particles to specific cells. One example for such targeting are antibodies directed against proteins enriched on the surface of cancer cells. In one embodiment the particle may have a ferromagnetic core. Such particles may be used in applications such as magnetic fluid hyperthermia (Jordan et al., Int J Hyperthermia, 12, 705-722, 1996).

In another embodiment the cargo molecule is a quantum dot. Coupling of the CPPs according to at least some embodiments of the present invention to the quantum dot may be achieved by covalent coupling, for example by amide bond formation between suitable functionalities on the peptide and the quantum dot or by non-covalent interactions, for example between a biotin moiety and a streptavidin molecule coupled to the quantum dot. In one example a cell-penetrating peptide is covalently linked to a quantum dot by elongation of the cell-penetrating peptide with a cysteine residue and coupling to amino-functionalized quantum dots using a heterobifunctional linker (S. Santra et al., Chem Comm, 2005, 3144-3146).

In another embodiment the cargo molecule is a short double-stranded oligodeoxynucleotide acting as a decoy molecule by specifically binding to transcription factors inside the cell. These decoy molecules are said to be taken up efficiently by cells without a need for specific carriers or delivery agents. According to at least some embodiments of the present invention, the efficiency and cytoplasmic delivery and/or tissue specificity may be further enhanced by conjugation to a CPP.

In a further embodiment the cargo molecule is an antibody. The manufacture of an antibody is known to the one skilled in the art and, for example, described in Harlow, E., and Lane, D., "Antibodies: A Laboratory Manual," Cold Spring Harbor Laboratory, Cold Spring Harbor, N.Y., (1988). Preferably, monoclonal antibodies may be used in connection with at least some embodiments of the present invention which may be manufactured according to the protocol of Kohler and Milstein and further developments based thereon. Antibodies as used herein, include, but are not limited to, complete antibodies, antibody fragments or derivatives such as Fab fragments, Fc fragments and single-stranded antibodies, as long as they are suitable and capable of binding to protein kinase N beta. Apart from monoclonal antibodies also polyclonal antibodies may be used and/or generated. The generation of polyclonal antibodies is also known to the one skilled in the art and, for example, described in Harlow, E., and Lane, D., "Antibodies: A Laboratory Manual," Cold Spring Harbor Laboratory, Cold Spring Harbor, N.Y., (1988). Preferably, the antibodies used for therapeutic purposes are humanized or human antibodies.

In a further embodiment the cargo molecule is a target specific binding peptide. Such peptides may be generated by using methods according to the state of the art such as phage display. Basically, a library of peptide is generated, such as in form of phages, and this kind of libraries is contacted with the respective target molecule. Those peptides binding to the target molecule are subsequently removed, preferably as a complex with the target molecule, from the respective reaction. It is known to the one skilled in the art that the binding characteristics, at least to a certain extent, depend on the particularly realized experimental set-up such as the salt concentration and the like. After separating those peptides binding to the target molecule with a higher affinity or a bigger force, from the non-binding members of the library, and optionally also after removal of the target molecule from the complex of target molecule and peptide, the respective peptide(s) may subsequently be characterized. Prior to the characterization optionally an amplification step is realized such as, e.g. by propagating the peptide coding phages. The characterization preferably comprises the sequencing of the target binding peptides. Basically, the peptides are not limited in their lengths, however, preferably peptides having a lengths from about 8 to 20 amino acids are preferably obtained in the respective methods. The size of the libraries may be about $10^2$ to $10^{18}$, preferably $10^8$ to $10^{15}$ different peptides, however, is not limited thereto.

Methods of Producing

According to at least some embodiments of the present invention, CPPs may optionally be produced according to any conventional means, including but not limited to chemical synthetic methods and recombinant biological methods.

In one embodiment, the invention provides a peptide which is a conservative amino acid substitution variant or a 90% homologous variant of AAAAEK or repeats of AAAAEK that substantially retains CPP activity.

In some embodiments, the isolated peptide fragments of AAAAEK and repeats thereof described herein are conservative amino acid substitution variants. In some instances, such peptides are at least 60% identical to a peptide of AAAAEK or repeats of AAAAEK, wherein the peptide variants retain CPP activity. Thus, one of skill in the art should consider carefully before modifying such amino acids. Substitutions or modifications to residues of this kind that maintain or enhance CPP activity is also encompassed within the scope of the terms "variant" and "derivative" as used in reference to peptides having the sequence of AAAAEK or repeats of AAAAEK.

The present invention further provides using the isolated nucleic acid molecules that encode the polypeptide having the fusion peptides and conservative nucleotide substitutions thereof, preferably in isolated form to generate the compositions of the invention. Conservative nucleotide substitutions include nucleotide substitutions which do not affect the coding for a particular amino acid as most amino acids have more than one codon. Conservative nucleotide substitutions therefore also include silent mutations and differential codon usage.

According to at least some embodiments the present invention is related to a nucleic acid coding for a CPP. Such nucleic acid can be easily derived by the ones skilled in the art based on the amino acid sequence of the peptide and the genetic code. It will be acknowledged that depending on the host organism the particular sequence can be adapted to the codon usage of the respective host organism.

According to at least some embodiments the present invention is related to a nucleic acid coding for a peptide, whereby said peptide comprises a CPP according to at least some embodiments of the present invention and a further peptide or protein, and whereby said protein is generally referred to as fusion peptides/proteins. According to protocols known to those skilled in the art this nucleic acid may either serve the expression and purification of recombinant proteins, in which at least one part comprise the CPP(s), and at least one other part as the further peptide or protein.

According to at least some embodiments, the present invention is related to a fusion protein as defined herein and more particularly to a fusion protein encoded by a nucleic acid coding for a fusion protein according to at least some embodiments of the present invention.

According to at least some embodiments the present invention is related to a composition comprising any of a complex, fusion molecule and/or conjugate according to at least some embodiments of the present invention, a composition comprising a peptide according to at least some embodiments of the present invention, a composition comprising a nucleic acid coding for a peptide according to at least some embodiments of the present invention, a composition comprising a peptide according to at least some embodiments of the present invention and a cargo molecule, a composition comprising a fusion protein, as DNA or RNA binding domain, according to at least some embodiments of the present invention and a composition comprising a nucleic acid coding for such fusion. It is within the skills of the one of the art that such compositions according to at least some embodiments of the present invention may comprise one or several of the peptides according to at least some embodiments of the present invention, one or several of the nucleic acids according to at least some embodiments of the present invention, and/or one or several of the cargo molecules. In connection therewith it is preferred that the term "several" means several different species of the respective compounds or molecules. It will be well acknowledged by the ones skilled in the art that the composition typically comprises a multitude of the individual species of the peptide according to at least some embodiments of the present invention, of the nucleic acid coding for such peptide and/or the of the cargo molecule.

A peptide of the present invention can be prepared according to a commonly known method of peptide synthesis, and substitution, addition or deletion can easily be achieved by changing the kind of protected amino acid. Special amino acids such as D-amino acid and sarcosine (N-methylglycine) may be introduced. Methods of peptide synthesis include, for example, solid phase synthesis, liquid phase synthesis; after the synthetic reaction, a peptide used in the present invention can be purified and isolated by combining ordinary methods of purification, for example, solvent extraction, distillation, column chromatography, liquid chromatography or recrystallization.

In one embodiment, the peptide of the invention can be prepared using standard solid phase (or solution phase) peptide synthesis methods, as is known in the art. In addition, the DNA encoding these polypeptides may be synthesized using commercially available oligonucleotide synthesis instrumentation and produced recombinantly using standard recombinant production systems. The production using solid phase peptide synthesis is necessitated if non-gene-encoded amino acids are to be included.

According to at least some embodiments of the present invention the CPP is attached to a cargo molecule. Such cargo molecule may be any cargo molecule as defined herein. The attachment can be either a fusion or a complex as defined above, such that the attachment may optionally be covalent or non-covalent, respectively, comprising at least one peptide according to at least some embodiments of the present invention and at least one cargo molecule. It is also within in the present invention that the attachment comprises more than one peptide according to at least some embodiments of the present invention, i.e. a plurality of such peptides, whereby the plurality of the peptides may comprise a plurality of the same or of different peptides. Also, the attachment according to at least some embodiments of the present invention may also comprise more than one cargo molecule, whereby the plurality of the cargo molecules may comprise a plurality of the same or of different cargo molecules.

In one embodiment, the attachment between the peptide(s) according to at least some embodiments of the present invention and the cargo molecule(s) is formed by covalent bonds. Such covalent bonds are preferably formed between either suitable reactive group of the peptide and the cargo and more preferable between a terminus of the peptide according to the present at least some embodiments of the invention and the cargo molecule(s). Depending on the chemical nature or the cargo molecules, the moiety, group or radical with which such covalent bond is formed varies and it is within the skills of a person of the art to create such bond.

In one embodiment, the covalent bond may be an amide bond formed between the carboxy group of the C-terminal amino acid of a peptide according to at least some embodiments of the present invention and the alpha amino group of the N-terminal amino acid of a peptide constituting a cargo molecule or vice versa.

In another embodiment, the covalent bond between the CPP and the cargo molecule can comprise a linker as described elsewhere elsewhere herein.

Alternatively, the attachment can be formed based on non-covalent bond(s). Such non-covalent bonds can be ionic bonds, hydrogen bonds or hydrophobic interaction or a combination of such bonds. In one embodiment such non-covalent bonds may be formed by a stretch of lysine residues, attached by covalent bonds to a peptide according to at least some embodiments of the present invention and the phosphate backbone of an oligonucleotide. Preferably the stretch of lysine consists of about 5 to 15 lysine residues.

Treatment

Peptides and peptide-cargo conjugates according to the present invention may be provided for use in a method of medical treatment. The medical treatment may preferably require delivery of the cargo molecule into a cell and optionally the nucleus of the cell.

Peptides and/or peptide-cargo conjugates are accordingly provided for use in treatment of disease. The use of a peptide and/or a peptide-cargo conjugate in the manufacture of a medicament for the treatment of disease is also provided. A method of treatment of a patient or subject in need of treatment for a disease condition is also provided comprising the step of administering a therapeutically effective amount of a peptide and/or a peptide-cargo conjugate to the patient or subject. Preferably, the cargo component of a peptide-cargo conjugate comprises an active agent (e.g. pharmaceutical agent) capable of treating, preventing or ameliorating the disease.

The present invention also provides for both prophylactic and therapeutic methods of treating a subject at risk of (or susceptible to) a disorder or having a disorder associated with aberrant or unwanted target gene expression or activity. "Treatment", or "treating" as used herein, is defined as the application or administration of a CPP-nucleic acid conjugate of the present invention (e.g., CPP-siRNA) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease. For siRNA, the treatment can include administering siRNAs to one or more target sites. The mixture of different siRNAs-CPP conjugates can be administered together or sequentially, and the mixture can be varied over time.

With regards to both prophylactic and therapeutic methods of treatment, such treatments may be specifically tailored or modified, based on knowledge obtained from the field of pharmacogenomics. The terms "pharmacogenomic(s)" and "pharmacogenetic(s)" are used herein interchangeably and, refer to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted target gene expression or activity, by administering to the subject a CPP-nucleic acid conjugate of the present invention (e.g., CPP-siRNA). Subjects at risk for a disease which is caused or contributed to by aberrant or unwanted target gene expression or activity can be identified by, for example, any or a combination of diagnostic or prognostic assays as described elsewhere herein.

Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined by one skilled in the art based on screening assays.

Another aspect of the invention pertains to methods of modulating target gene expression, protein expression or activity for therapeutic purposes. Accordingly, in an exemplary embodiment, the modulatory method of the invention involves contacting a cell capable of expressing target gene with a CPP-nucleic acid conjugate of the present invention (e.g., CPP-siRNA) that is specific for the target gene or protein (e.g. if the nucleic acid is a siRNA, then the siRNA is specific for the mRNA encoded by said gene or specifying the amino acid sequence of said protein) such that expression or one or more of the activities of target protein is modulated. These modulatory methods can be performed in vitro (e.g., by culturing the cell with the conjugate) or, alternatively, in vivo (e.g., by administering the conjugate to a subject). As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

The CPP-nucleic acid conjugate of the present invention can be administered to individuals to treat (prophylactically or therapeutically) disorders associated with aberrant or unwanted target gene activity. In conjunction with such treatment, "pharmacogenomics" or "pharmacogenetics" (both terms are used interchangeably) (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons. See, for example, Eichelbaum et al. Clin. Exp. Pharmacol. Physiol. 23:983-985 (1996) and Linder et al. Clin. Chem. 43: 254-266 (1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms.

The compositions of the invention can act as novel therapeutic agents for controlling a variety of diseases and disorders. For example, the composition can be used as a therapeutic against one or more of cellular proliferative and/or differentiative disorders, disorders associated with bone metabolism, immune disorders, hematopoietic disorders, cardiovascular disorders, liver disorders, kidney disorders, muscular disorders, haematological disorders, viral diseases, pain or neurological disorders, or metabolic disorders. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative", and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

"Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, kidney, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) CritRev. in Oncol. 1Hemotol. 11: 267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and "Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

The compositions of the invention can be used to treat a variety of immune disorders, in particular those associated with overexpression of a gene or expression of a mutant gene. Examples of hematopoietic disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosus, autoimmunethyroiditis, dermatitis (including atopic dermatitis and eczematous dermatitis), psoriasis, Sjgren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Examples of disorders involving the heart or "cardiovascular disorder" include, but are not limited to, a disease, disorder, or state involving the cardiovascular system, e.g., the heart, the blood vessels, and/or the blood. A cardiovascular disorder can be caused by an imbalance in arterial pressure, a malfunction of the heart, or an occlusion of a blood vessel, e.g., by a thrombus. Examples of such disorders include hypertension, atherosclerosis, coronary artery spasm, congestive heart failure, coronary artery disease, valvular disease, arrhythmias, and cardiomyopathies.

Disorders which may be treated by methods described herein include, but are not limited to, disorders associated with an accumulation in the liver of fibrous tissue, such as that resulting from an imbalance between production and degradation of the extracellular matrix accompanied by the collapse and condensation of preexisting fibers.

Additionally, molecules of the invention can be used to treat viral diseases, including but not limited to hepatitis B, hepatitis C, herpes simplex virus (HSV), HIV-AIDS, poliovirus, and smallpox virus. Molecules of the invention are engineered as described herein to target expressed sequences of a virus, thus ameliorating viral activity and replication. The molecules can be used in the treatment and/or diagnosis of viral infected tissue. Also, such molecules can be used in the treatment of virus-associated carcinoma, such as hepatocellular cancer.

Pharmaceuticals

The invention pertains to uses of the CPP of the invention for therapeutic treatments as described elsewhere herein. Thus, the scope of the invention extends to the use of a CPP of the invention for the manufacture of a medicament (or pharmaceutical) for treating or preventing a disorder as described elsewhere herein. Accordingly, the CPP of the present invention can be incorporated into compositions, preferably pharmaceutical compositions, suitable for administration. Such compositions typically comprise at least one conjugate according to the present invention or a mixture of conjugates and optionally, a pharmaceutically acceptable carrier. As used herein "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A composition of the invention, preferably pharmaceutical composition, is formulated to be compatible with its intended route of administration. Examples of routes of administration include parenteral, e.g., intravenous, intradermal, subcutaneous, intraperitoneal, intramuscular, oral (e.g., inhalation), transdermal (topical), transmucosal, intraocular, and intratumoral administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CremophorEL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems.

Biodegradable, biocompatible polymers can be used, such as ethylene vinyl acetate, polyanhydrides, polyglycolic acid, collagen, polyorthoesters, and polylactic acid.

Methods for preparation of such formulations will be apparent to those skilled in the art. The materials can also be obtained commercially from Alza Corporation for example and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

It is furthermore understood that appropriate doses of a composition depend upon the potency of composition with respect to the expression or activity to be modulated. When one or more of these conjugates of the invention is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Synthesis of Cell Penetrating Peptides for Drug Delivery and Stem Cell Applications The results presented herein relate to a novel short CPP (<10-mer) that exhibits cell penetrating activity not only in soluble conditions but also in gel-like conditions. The CPP X (PepX) having the sequence AAAAEK(A) increased cellular uptake of multiple peptides in a synergistic manner when combined with other molecules.

Briefly, dye-labeled model (bioactive) peptide A (PepA) was modified with small molecules or with a desired CPP and the uptake efficiencies of these molecules were studied in mammalian cells. The results suggest that PepA internalization synergistically improved when PepX was combined with other molecules. Furthermore, PepX improved the solubility of the final product. It was also observed that CPP PepX incorporating molecules stayed in the cytosol of neural stem cells for up to 5 months in culture conditions while the cells are undergoing differentiation and allows increased derivation of neurons.

The materials and methods employed in the experiments disclosed herein are now described.

Synthesis

Bioactive (model) peptide A (PepA) and CPP X (PepX) were synthesized via solid phase peptide synthesis (SPPS) methods (Suh et al., 2001 Comprehen. Biomat 4: 219-245; Suh et al., 2013 Polymer Adhesion, Friction and Lubrication 283-317 (Wiley)). Fmoc-deprotection was performed with organic bases such as 4-methyl piperidine and DBU in DMF at room temperature. Coupling reaction was performed in the presence of Fmoc-protected amino acids with the mixture of coupling reagents and organic bases (e.g., HBTU, HOBt and DIEA). The cleaved peptide from the resin was purified by HPLC, collected, and stored for future uses. HEK293 and ReNcell VM cell lines were maintained and utilized for cellular experiments. Live-Cell imaging analysis was performed on an Olympus IX81 and IX83-DSU widefield spinning disc confocal microscope equipped with an LCI Chamlide stage-top incubator unit.

The results of the experiments presented in this Example are now described.

Synthetic Cell Penetrating Peptide (CPP) AAAAEK Conjugated to a Bioactive Lipid (i.e., Retinoic Acid)

Figure 2:
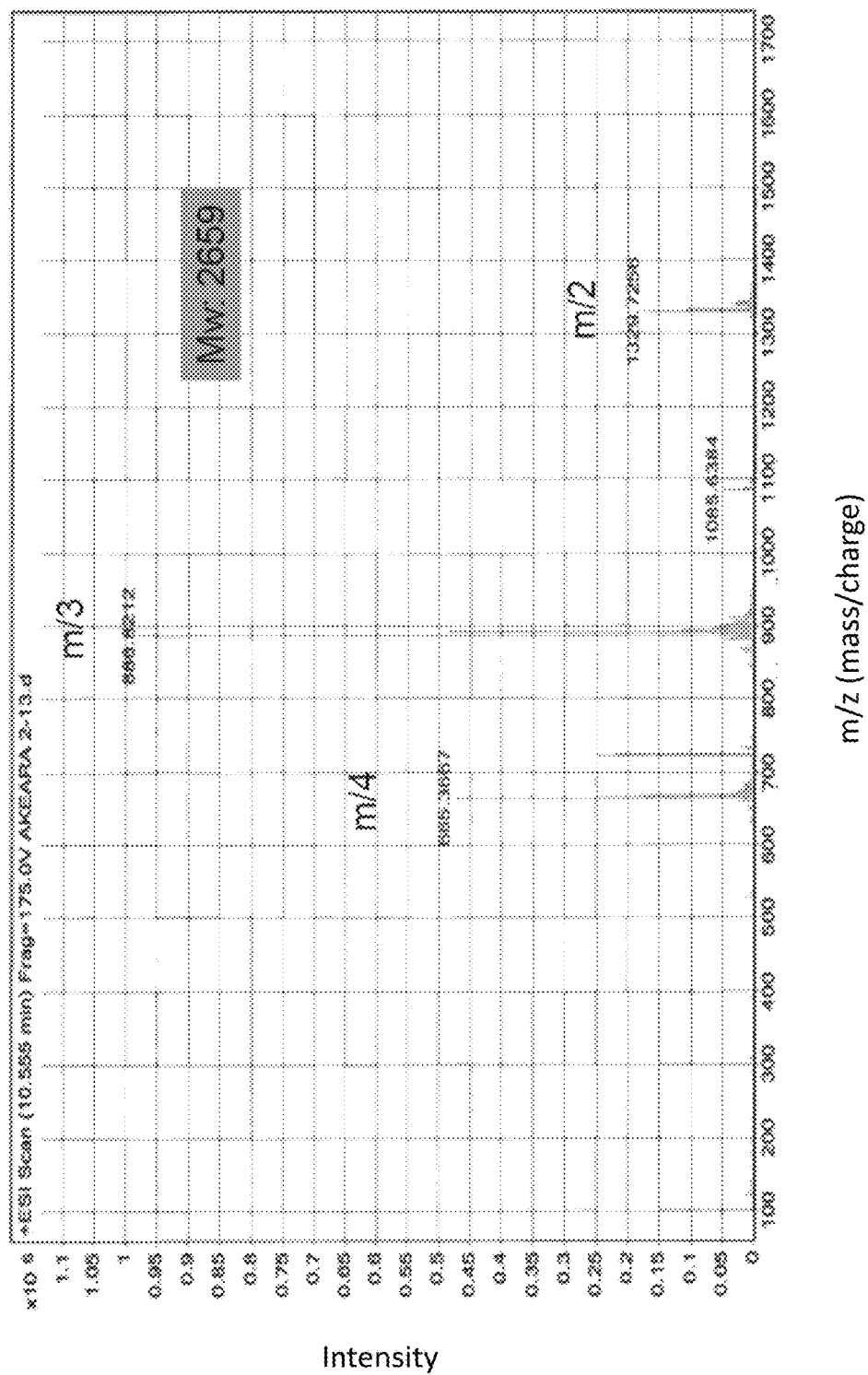
FIG. 2 is an image depicting the molecular weight of RA-ROX-AKEA analyzed by ESI-TOF-MS.
Figure 3:
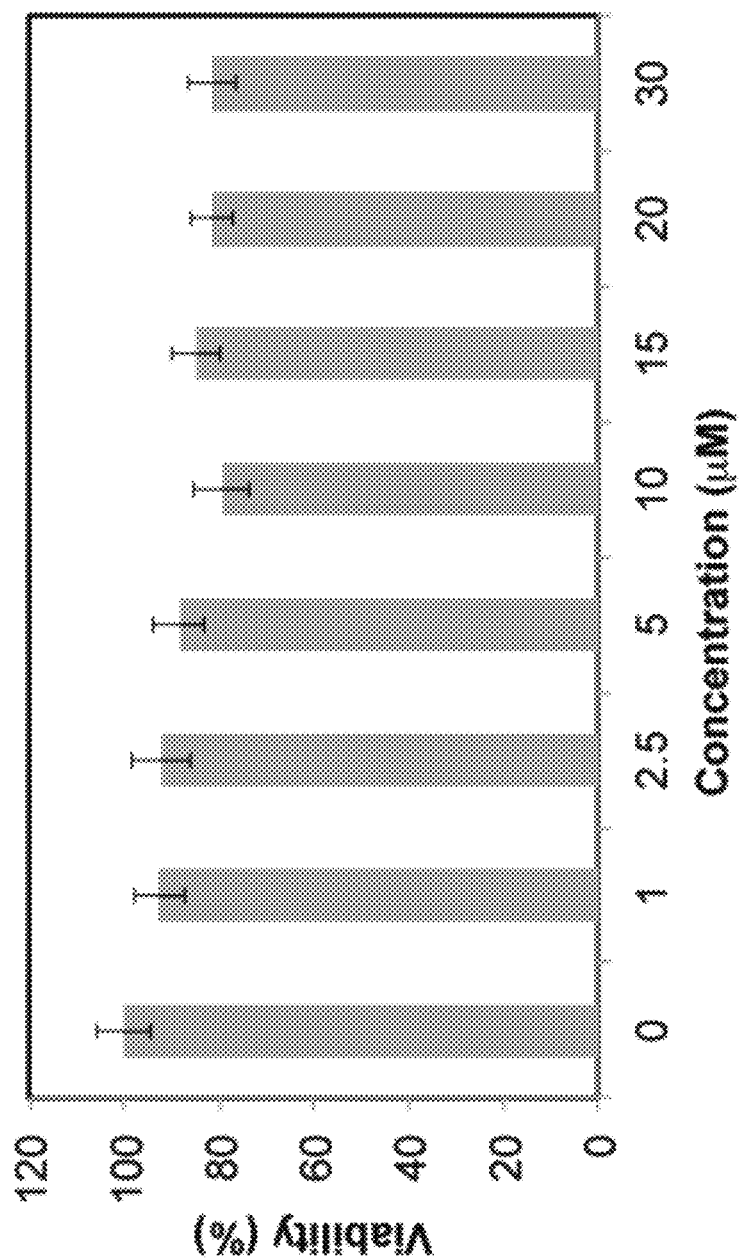
FIG. 3 is a graph demonstrating the cytotoxicity of RA-ROX-AKEA on a neural stem cell (ReNcell VM). ReNcell VM was incubated for 24 hrs in the presence of RA-ROX-AKEA.
Figure 4:
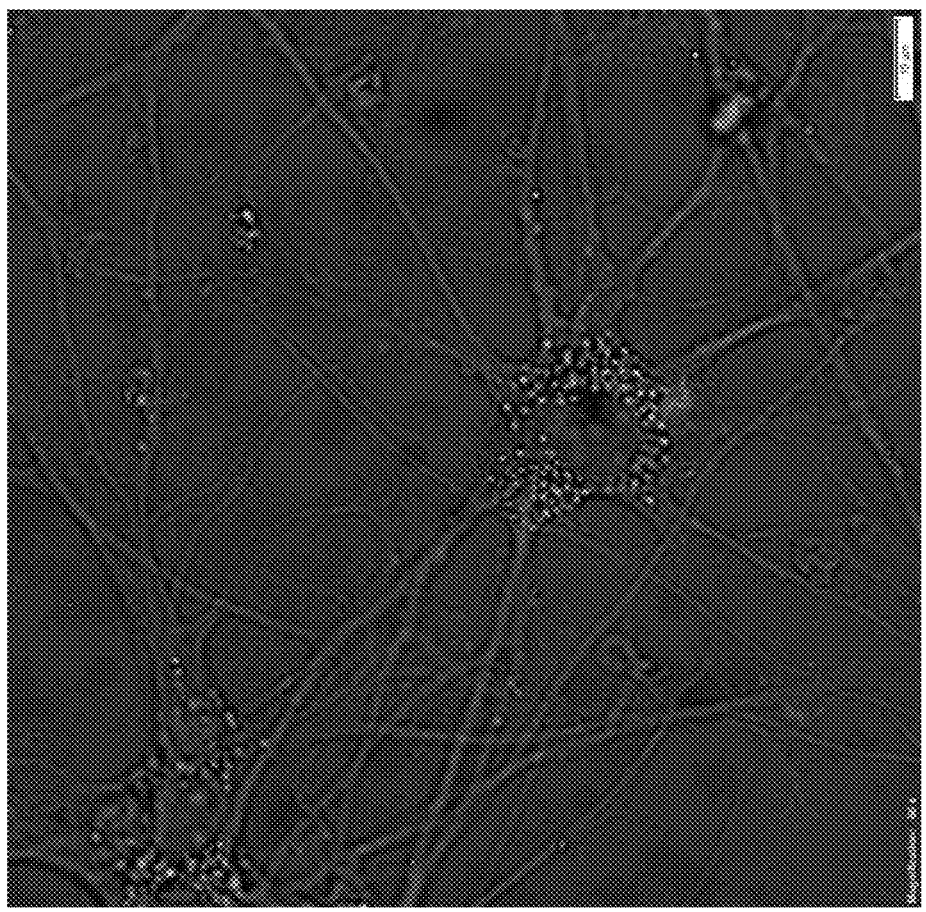
FIG. 4 is an image depicting a live-cell image of a neural stem cell (ReNcell VM). 10 µM of RA-ROX-AKEA was treated on the cells and maintained for 122 days (4 months) without additional treatment of RA-ROX-AKEA.
Figure 5:
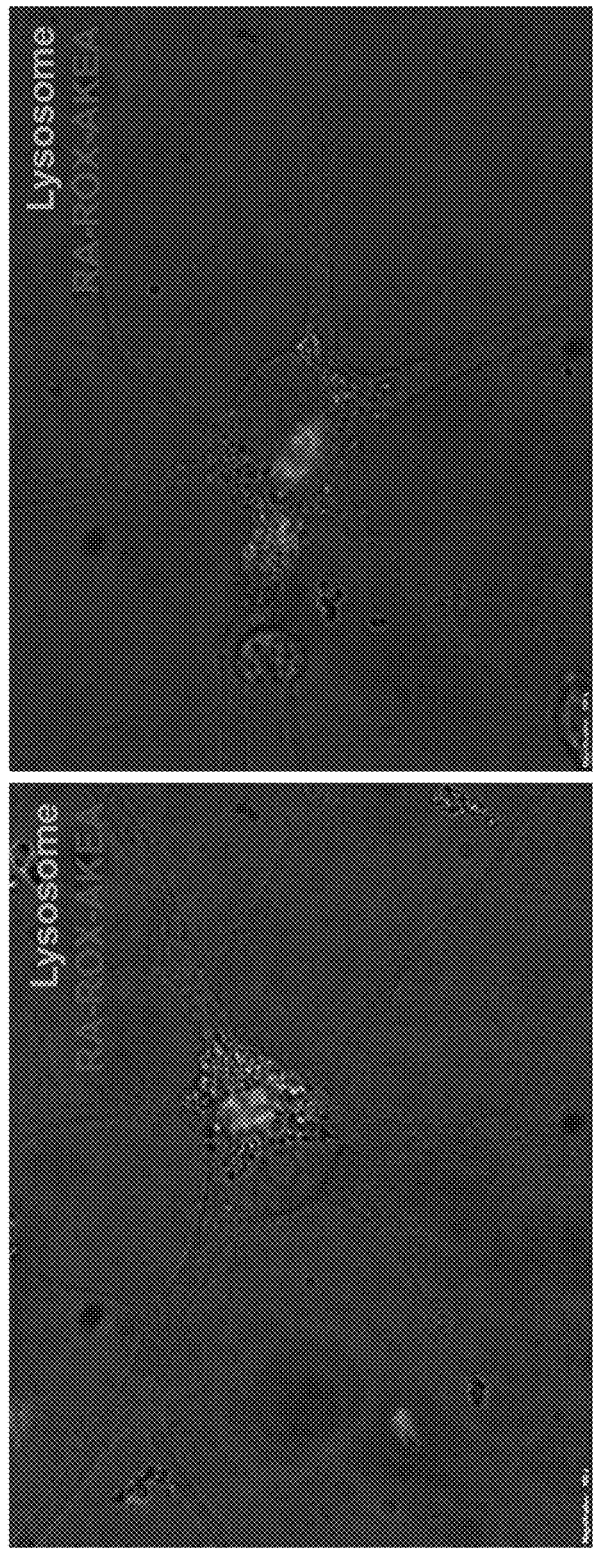
FIG. 5 is a series of images depicting a live-cell image of RA-ROX-AKEA Treated ReNcell VM. RA-ROX-AKEA distributed out of the lysosome after 3 months of the cellular uptake. Lysosome was labeled with CellLight® Lysosomes-GFP (Life Technologies).
Figure 6:
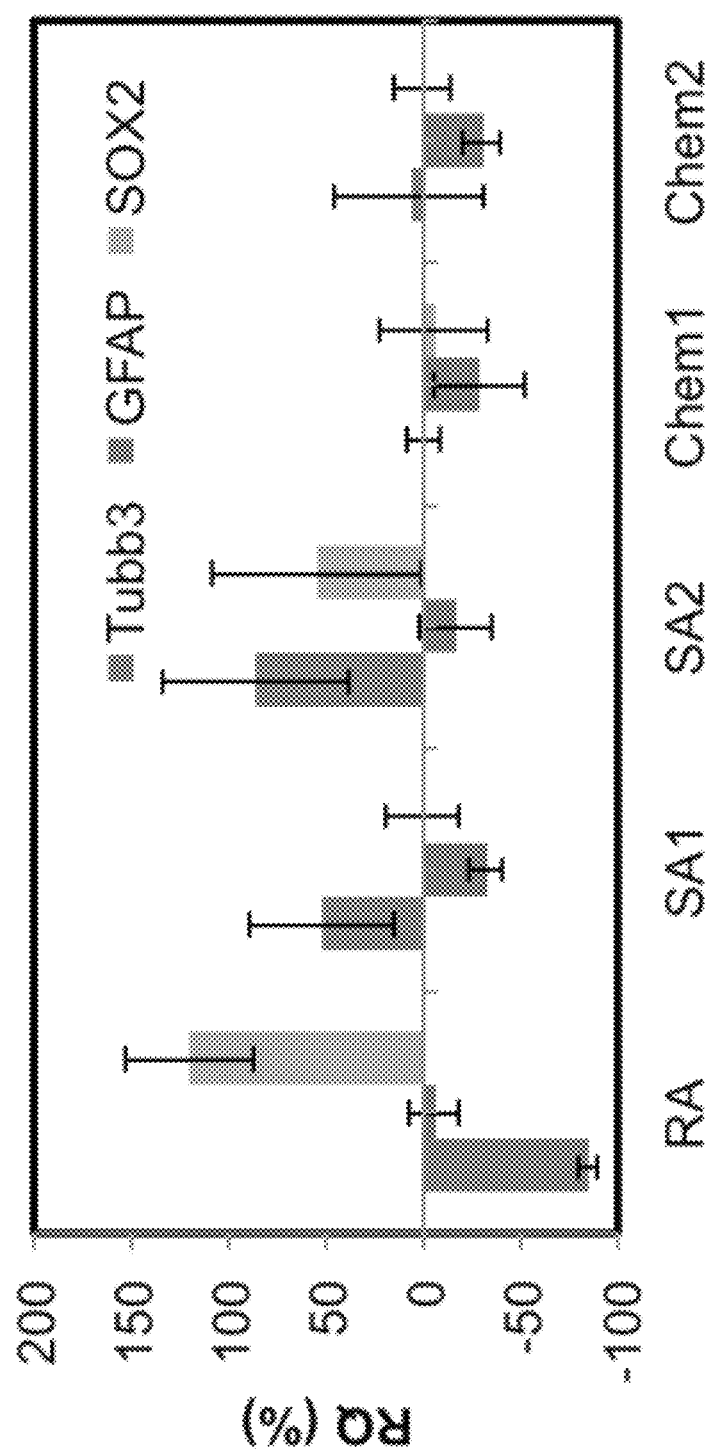
FIG. 6 is a chart depicting RT-qPCR results of RA-ROX-AKEA incorporating synthetic CPP agent. Differentiated stem cells were cultured for 10 weeks. The results are in comparison to control cells differentiated without growth factors. RA=Retinoic acid (Highly cytotoxic; low cell count among results), SA1=RA-ROX-AKEA, SA2=RA-FAM-$(A_4EK)_3A$ (Synthetic CPP Agents), Chem1=interferon gamma, Chem2=lithium chloride.

FIG. 1 shows the chemical structure of RA-ROX-$(A_4EK)_3A$ (referred herein as RA-ROX-AKEA), which is composed of three parts; repeated sequence of AAAAEK, fluorophore to label the synthetic peptide (Li, Y.; Glazer, A. N. Bioconjugate Chemistry 1999, 10, 241; Suwal, S.; Pflum, M. K. H. Angewandte Chemie 2010, 122, 1671, and retinoic acid (RA), which is bioactive lipid known to induce neuronal differentiation of adult stem cells (Akita, et al., Brain Research 2002, 954, 286; Anjomshoa, et al., Stem Cells and Development 2009, 18, 259; Coyle, et al., PloS one 2011, 6; Elizalde, et al., Stem Cells 2011, 29, 141; Engberg, et al., Stem Cells 2010, 28, 1498). Due to the ionizable moieties (i.e., Glu-Lys) embedded in the whole sequence, RA-ROX-AKEA has increased water-solubility showing no aggregation even at high concentrations (e.g., 300 µM). This synthetic peptide with the molecular weight of 2659 (FIG. 2) exhibited no considerable cytotoxicity up to the concentration of 30 µM when tested on ReNcell VM cells, a commercial neural stem cell line (FIG. 3) (Donato et al., BMC neuroscience 2007, 8, 36; Lange et al., Neuroscience letters 2011, 488, 36). Interestingly, the treatment of RA-ROX-AKEA for only one day was sufficient to enable cellular uptake. It was also observed that the internalized RA-ROX-AKEA can stay in the cytosolic region for up to 4 months even after multiple media changes without further treating with RA-ROX-AKEA (FIG. 4). Live-Cell imaging showed that ReNcell VM cells incorporating RA-ROX-AKEA molecules were still alive and the active movements of the cells implies that the internalized RA-ROX-AKEA molecules induced no obvious harmful effects on ReNcell VM cells. FIG. 5 shows the cellular distribution of RA-ROX-AKEA after internalization into ReNcell VM. Lysosome was labeled with CellLight® Lysosomes-GFP (Benjaminsen, et al., Molecular Therapy 2013, 21, 149; Marrache, et al., Proceedings of the National Academy of Sciences 2012, 109, 16288), whereby the final destination of the endocytic pathway showed no overlap with RA-ROX-AKEA (labeled red) implying the possibility of the escape of RA-ROX-AKEA molecules out of the endosomal or lysosomal compartments (FIG. 5). RT-qPCR experiments were also conducted and it was confirmed that ReNcell VM cultured with RA-ROX-$(A_4EK)_3A$ and RA-FAM-$(A_4EK)_3A$ both included increased neuronal differentiations (FIG. 6).

Reverse Transcription Polymerase Chain Reaction (RT-PCR) Analysis

Total mRNA was extracted using mRNA isolation kit (Ambion, Life Technologies) according to the manufacturer's protocol. For higher yield, neural stem cells from eight wells in the same culture plate were homogenized in cell lysis buffer.

Concentrations of mRNA samples were evaluated based on $OD_{260}/OD_{280}$. mRNA samples were reverse transcribed using reverse transcription kit (Applied Biosystems). PCR amplification of cDNA was carried out using universal PCR master mix (Applied Biosystems) and gene-specific primer sets (Applied Biosystems). These primers included neural stem cell (Nestin, SOX2), immature neuron (Tubb3), mature neuron (MAP2), and astrocyte (GFAP) specific genes. GAPDH was used as a control (house keeping gene). The cycles for RT-PCR consisted of 1 second denaturation at 95° C., 20 second annealing at 60° C. RT-PCR products were analyzed using Mastercycler ep realplex 4 (Eppendorf).

Figure 12:
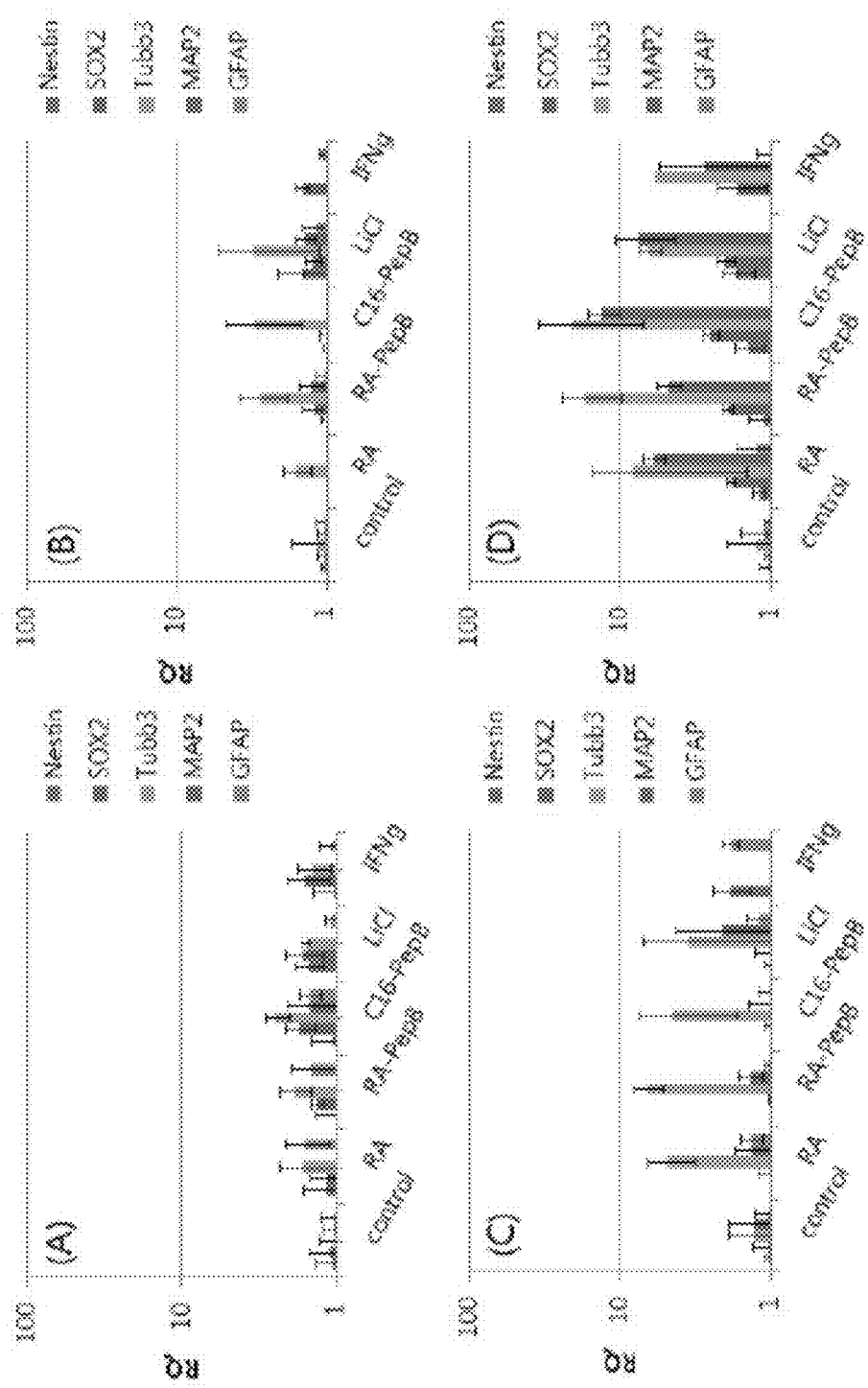
FIG. 12, comprising
Figure 13:
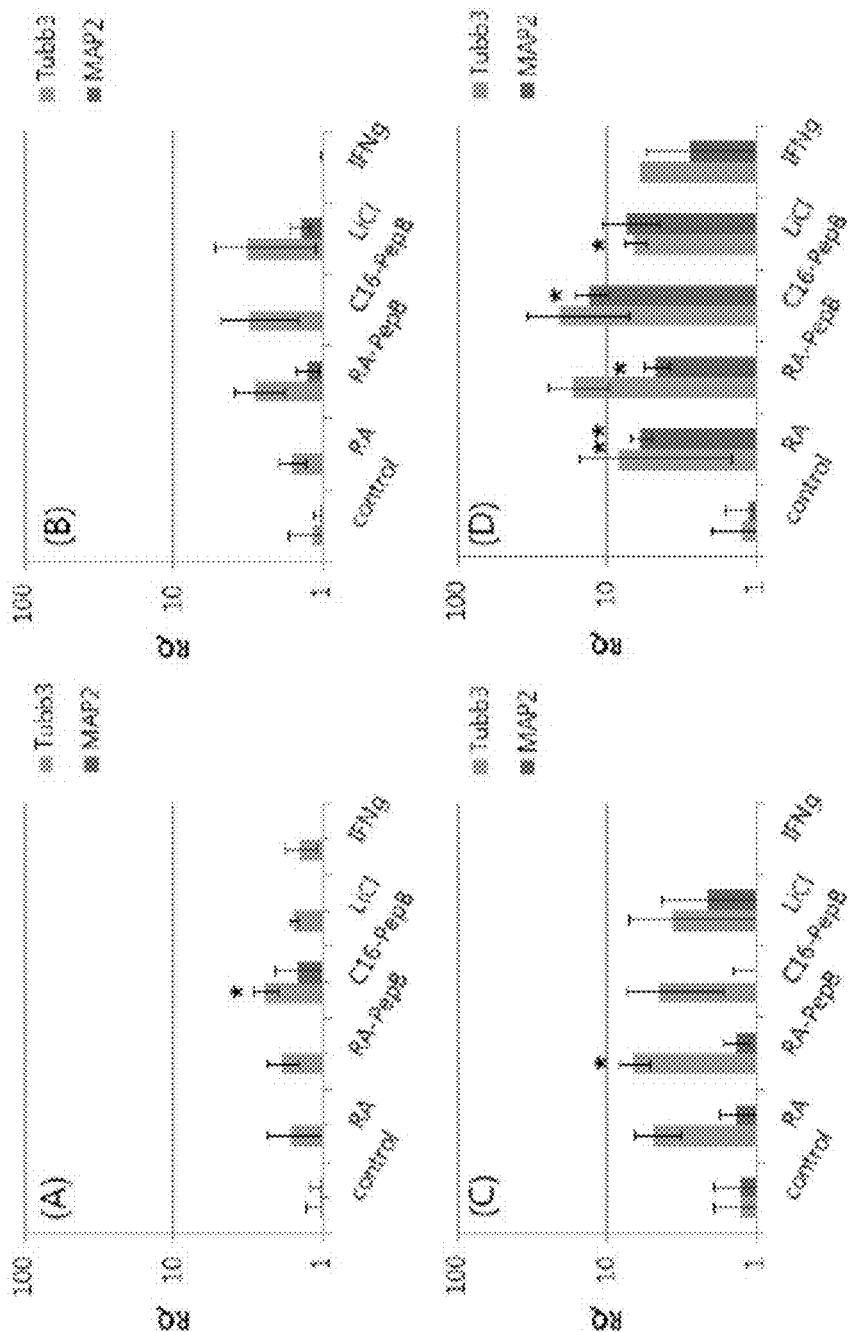
FIG. 13, comprising

Quantitative real-time PCR (qRT-PCR) analysis of neural stem cell (Nestin, SOX2), early neuron (Tubb3), mature neuron (MAP2), and astrocyte (GFAP)-specific gene expression in ReNcell VM was evaluated after treatment with chemicals including RA, RA-PepB (PepB is also referred herein as PepX), C16-PepB, LiCl and IFNγ. It was confirmed that cells cultured with PepB increased neuronal differentiations (FIGS. 12 and 13).

Synthetic Cell Penetrating Peptide (CPP) AAAAEK Conjugated to a Model Bioactive Peptide (i.e., PepA=ASVKEYPSRDT): SEQ ID NO: 2.

Figure 7:
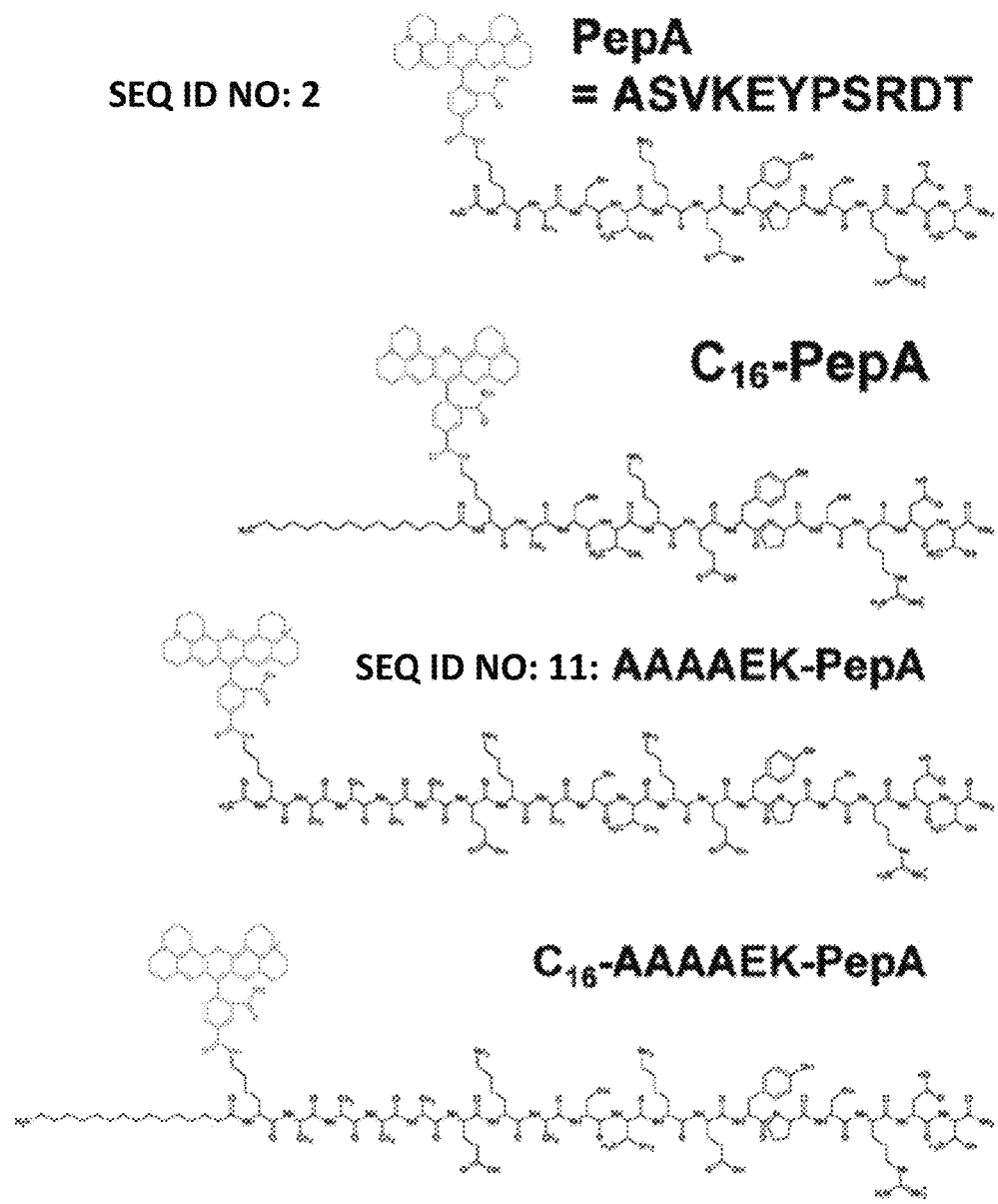
FIG. 7 is a schematic depicting chemical structures of model bioactive peptide A (PepA).
Figure 8A:
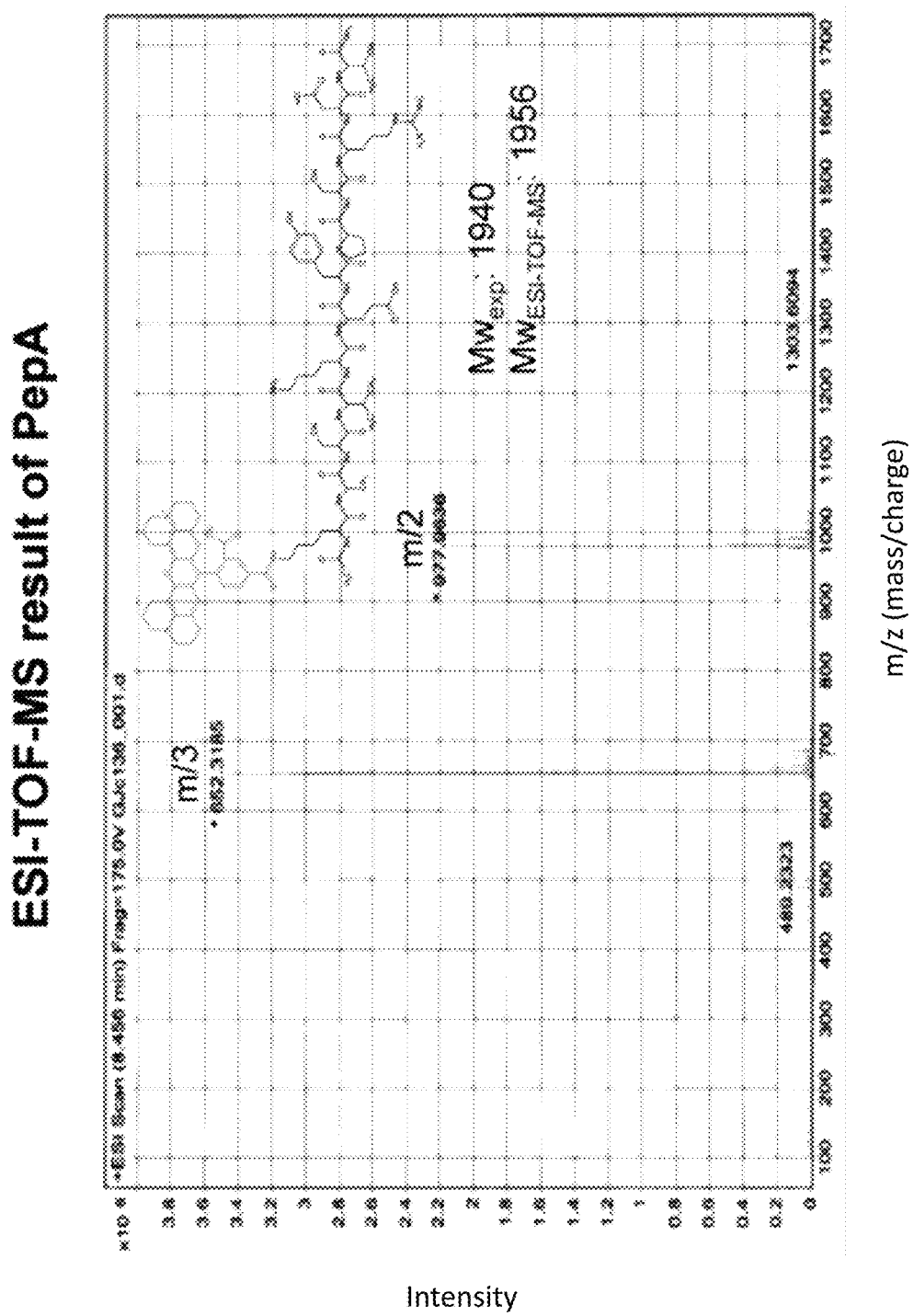
FIGS. 8A and 8B, is a series of imaged depicting molecular weight of model bioactive peptide A (PepA) analyzed by ESI-TOF-MS.
Figure 8B:
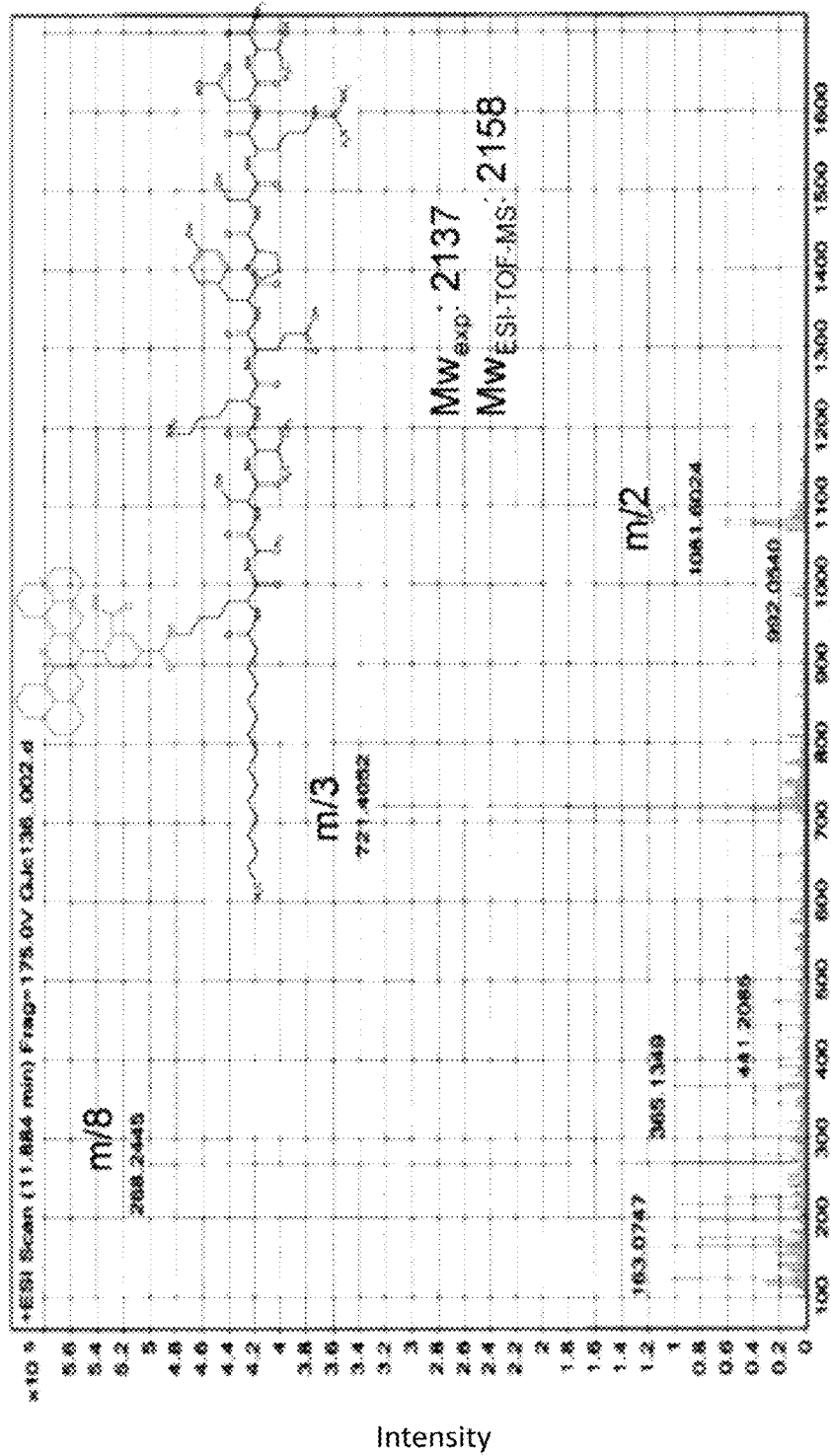
Figure 9:
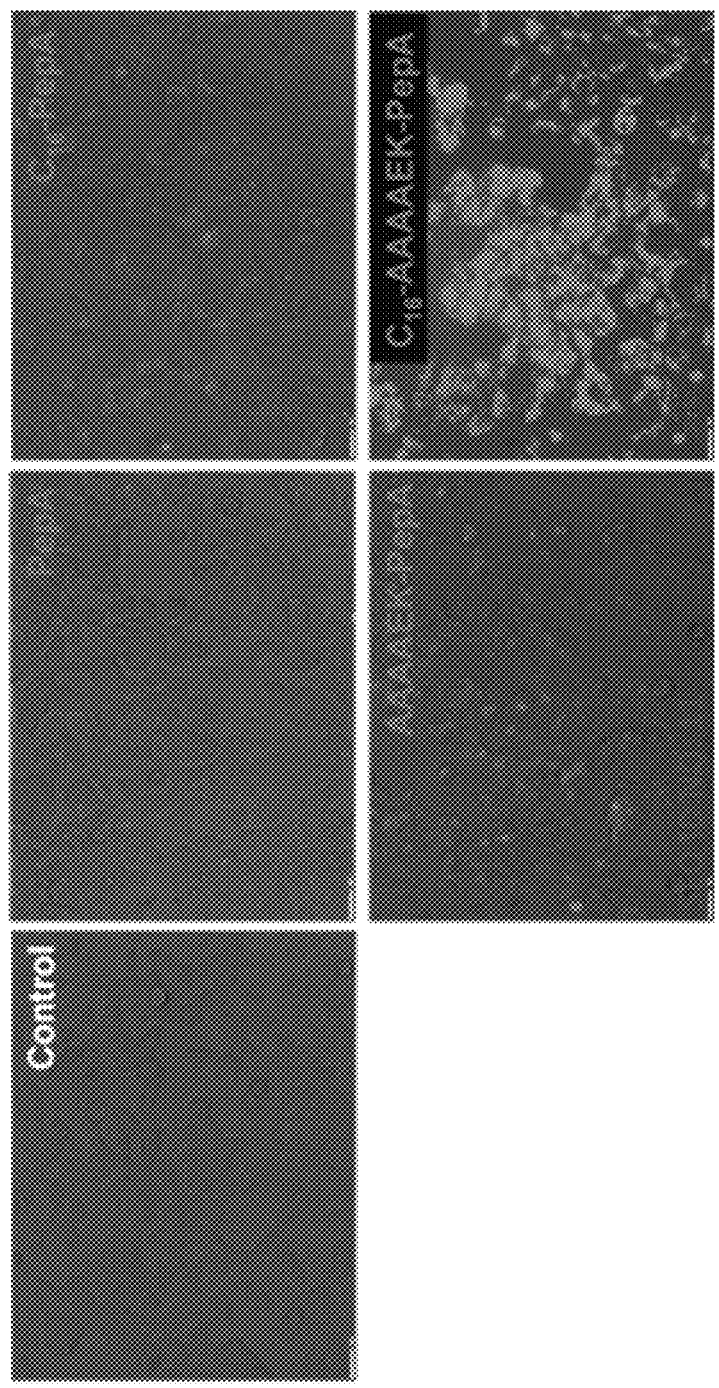
FIG. 9 is a series of images depicting live-cell uptake of bioactive peptide A (PepA) labeled with the ROX Dye. Bioconjugation with palmitic acid (C16 tail) and/or CPP AAAAEK (PepX) attachments increased cellular uptake in HEK293 cultures.
Figure 10:
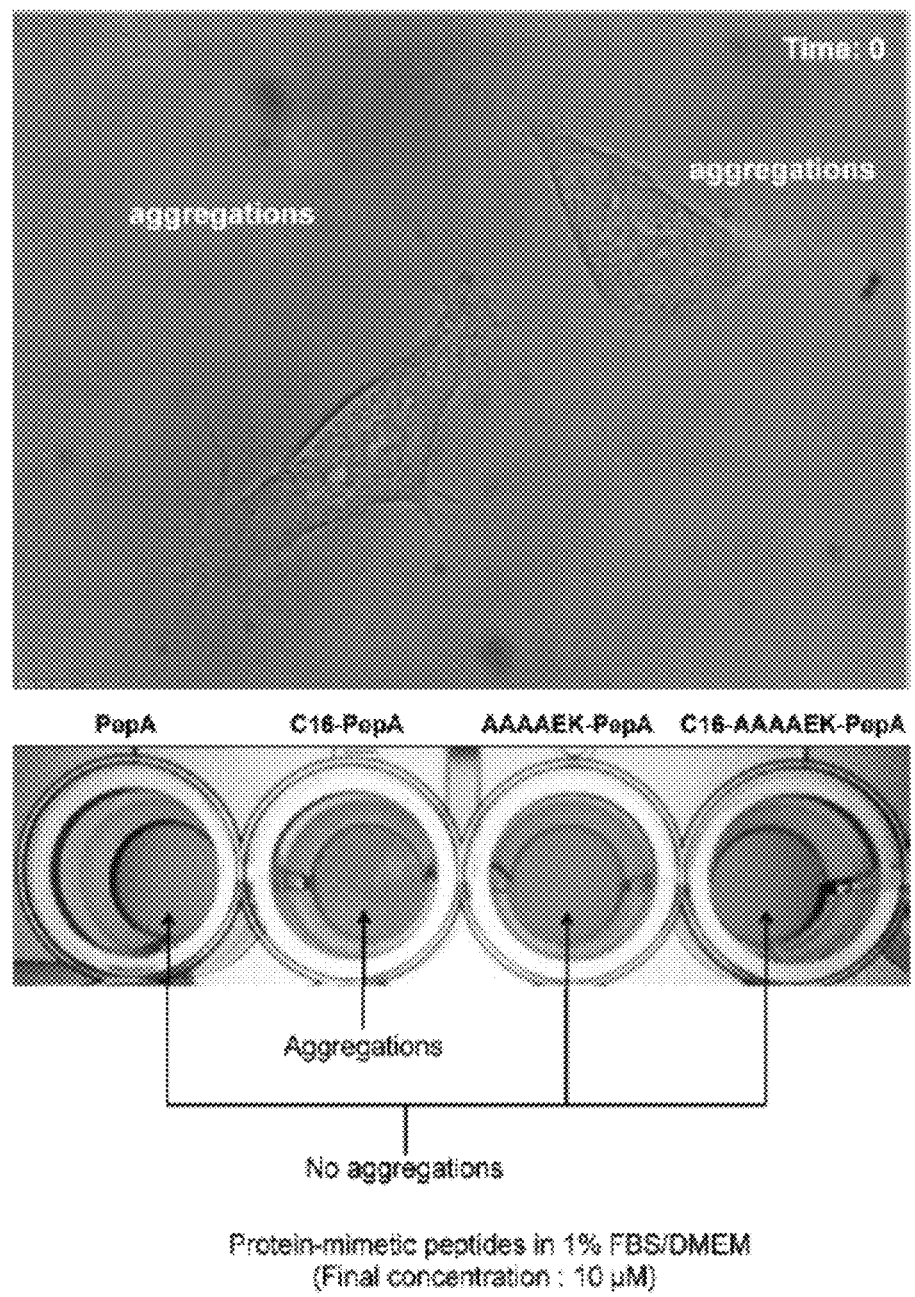
FIG. 10 is a series of images showing solubility of a model bioactive peptide (PepA) derivatives. Images of HEK293 after solubilizing into cell culture media (DMEM supplemented by 1% FBS). Lipidation of PepA peptide showed severe aggregation in cell culture media (C16-PepA).
Figure 11:
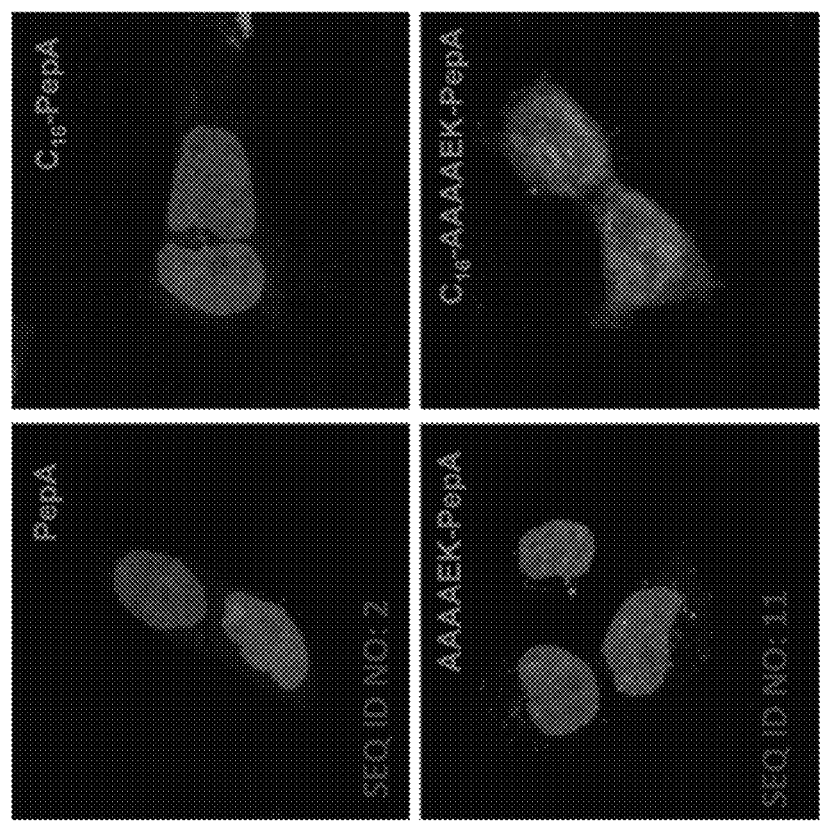
FIG. 11 is a series of images depicting laser-scanning confocal microscope imaging of bioactive peptide A (PepA) labeled with the ROX dye. Bioconjugation with palmitic acid (C16 tail) and/or CPP AAAAEK (PepX) attachments increased cellular uptake in HEK293 cultures. AAAAEK-PepA incorporated well dispersed inside the cell. C16-AAAAEK-PepA incorporation was substantially more than all other samples.

Results presented elsewhere herein showed the delivery of a bioactive lipid via the AAAAEK sequence into neural stem cells. The next set of experiments were designed to use a model bioactive peptide A (PepA) having a sequence of $H_2N$-ASVKEYPSRDT-COOH (Strehl, et al., Arthritis and Rheumatism 2011, 63, 3779; Kosugi et al., PLoS ONE 2011, 6(11), e28234. doi:10.1371/journal.pone.0028234) (FIGS. 7, 8) and to test its uptake in HEK293 cells (a non-stem cell example) as (FIGS. 9-11). The goal of the experiments was to show that the AAAAEK sequence allows PepA to enter the cells. Further experiments can be designed to test the AAAAEK peptide's cell penetrating capabilities to other peptides appearing in the literature (Strehl, et al., Arthritis and Rheumatism 2011, 63, 3779; Kosugi et al., PLoS ONE 2011, 6(11), e28234. doi:10.1371/journal.pone.0028234).

Example 2: RA-PepB Sub-Cellular Localization Study (2D)

It was initially observed that PepB molecules ended up inside the cytosol. Specifically, it was observed that PepB molecules went through the endosomal pathway and then through the lysosome but it was also observed that they were outside the lysosome (still inside the cytosol). Experiments therefore were designed to perform mitochondrial sub-cellular localization for further investigation. Briefly, ROX dye(red)-labeled RA-PepB (1 µM) was treated onto neural stem cells (ReNcell VM) for 4 weeks and then cultured for another 8 weeks (12 week total). After the 12 week time point (3 months) cultured cells were stained with CellLight Mito-GFP (Thermo Fisher Scientific; green fluorescent) via a viral technique. RA-PepB localized onto mitochondria compartment (yellow dots) as evident in FIG. 14. The co-localization profile, however, was not 100% since some sub-cellular compartments in FIG. 14 are red (showing only red fluorescent dye labeled RA-PepB). This new finding allows for using PepB constructs to target diseases and injuries (long-term) that affect the mammalian cell mitochondria, which is an important sub-cellular component.

Example 3: Gene Expression Analysis of PepB Treated Neural Stem Cells (2D)

Figure 15:
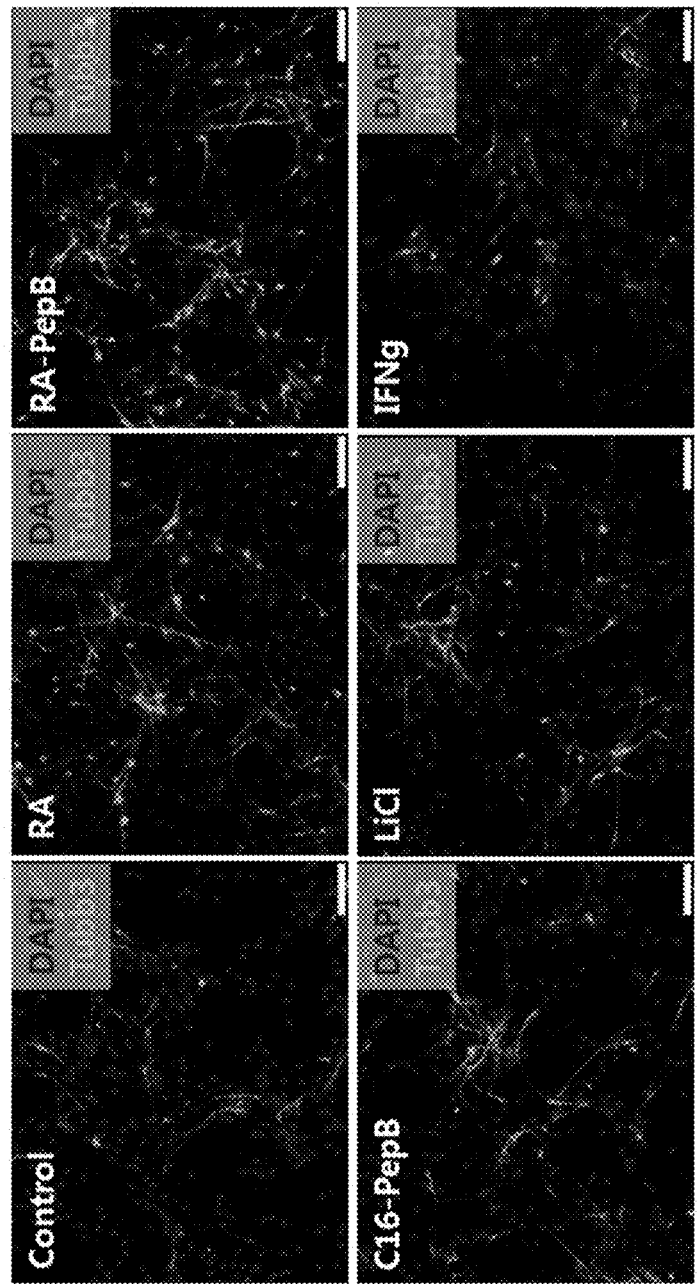
FIG. 15. Tubb3 Expression Analysis for 4-Week Differentiated ReNcell VM Cells. ReNcell VM cells were treated with neural stem cell culture medium (control), RA (retinoic acid), RA-PepB, C16-PepB, LiCl, and IFNγ (interferon gamma). Tubb3 proteins expressed in the cells were stained as green and cell nuclei were stained with blue (DAPI).
Figure 16:
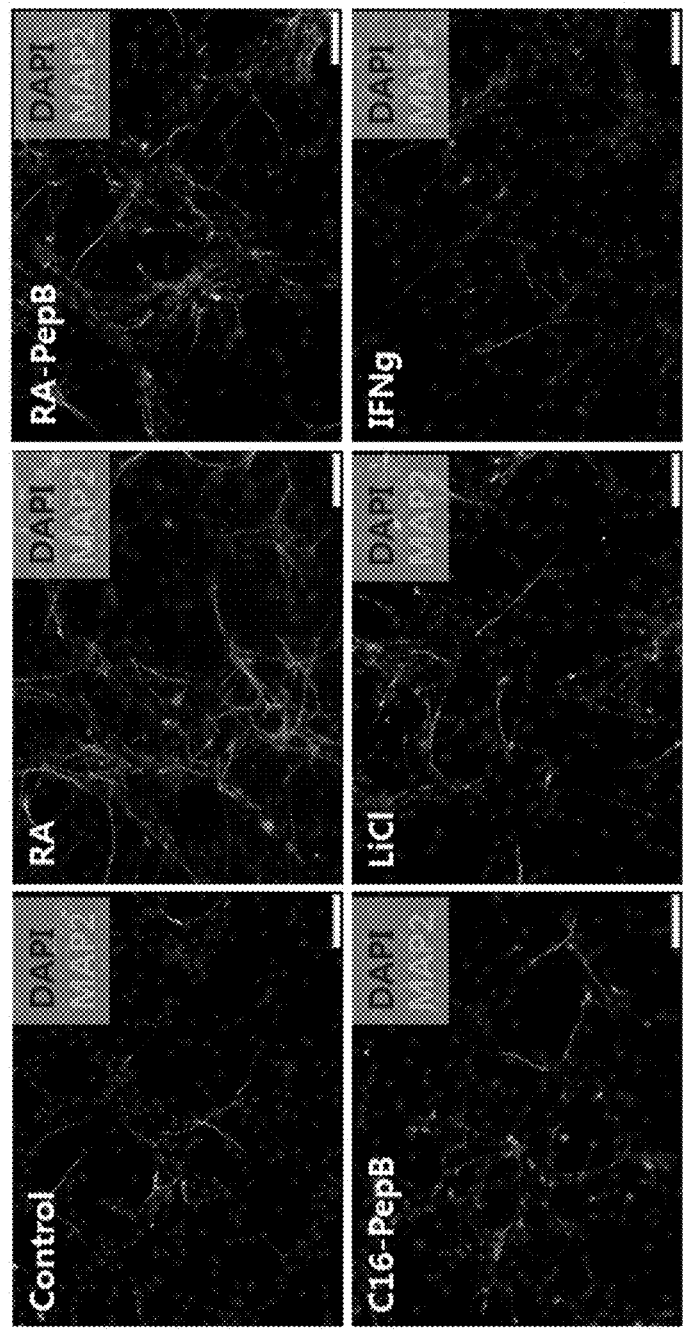
FIG. 16. MAP2 Expression Analysis for 4-Week Differentiated ReNcell VM Cells. ReNcell VM treated with cell culture media (control), RA, RA-PepB, C16-PepB, LiCl, and IFNγ (interferon gamma). MAP2 proteins expressed in the cells were stained as green and cell nuclei were stained with blue (DAPI) FIG. 17. Quantitation of Immunocytochemistry Results for Tubb3/MAP2 Proteins. Relative numbers of the cells expressing Tubb3 and MAP2 proteins were counted and normalized to the control group (*P<0.05, **P<0.01).
Figure 17:
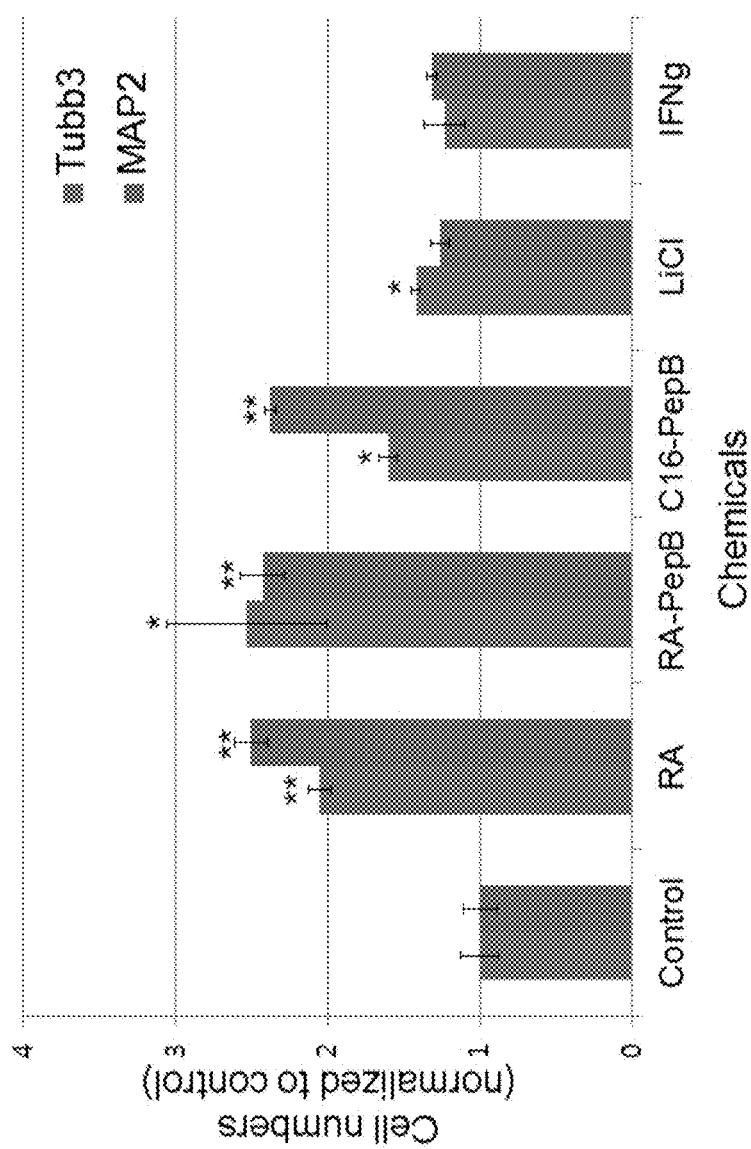

The proteins expressed in ReNcell VM cells were visualized with antibodies to study the protein expression by the differentiation of the stem cells in the presence of various soluble factors including RA-PepB and C16-PepB. Neural marker proteins such as Tubb3 (early neuronal-specific protein) (FIG. 15) and MAP2 (mature neuronal-specific protein) (FIG. 16) were stained and visualized on a fluorescent microscope. As is shown in FIGS. 15 and 16, Tubb3 or MAP2 expression levels in 4-week differentiated ReNcell VM cells were evaluated via immunocytochemistry (ICC). Protein expression, after antibody staining, was visualized and quantitatively compared by counting Tubb3 or MAP2-positive cells. ReNcell VM cells treated with RA, RA-PepB, C16-PepB and LiCl showed statistically significant increases in Tubb3 expression compared to the control (FIG. 17). Statistically significant increases in MAP2 expression were observed for RA, RA-PepB, and C16-PepB-treated groups (FIG. 17). The ICC results support the idea that PepB derivatives have an ability to induce ReNcell VM differentiation into cells with neuronal markers.

Example 4: RA-PepB Internalization Study in Three-Dimensional Hydrogels (3D)

Experiments were designed to evaluate RA-PepB in a 3D setting.

Cell Encapsulation in Calcium Alginate Hydrogels

Experiments were designed to develop a PepB technology so that they can be utilized in not only two dimensional conditions but also three dimensional environments such as tissue constructs and two three-dimensional synthetic matrices for achieving neuronal differentiation of human neural stem cells. One prime candidate is the utilization of calcium alginate hydrogels. It is important that in such matrices, biomacromolecules such as growth factors, peptides, and small therapeutics get to the cellular sources, such as stem cells.

Figure 18:
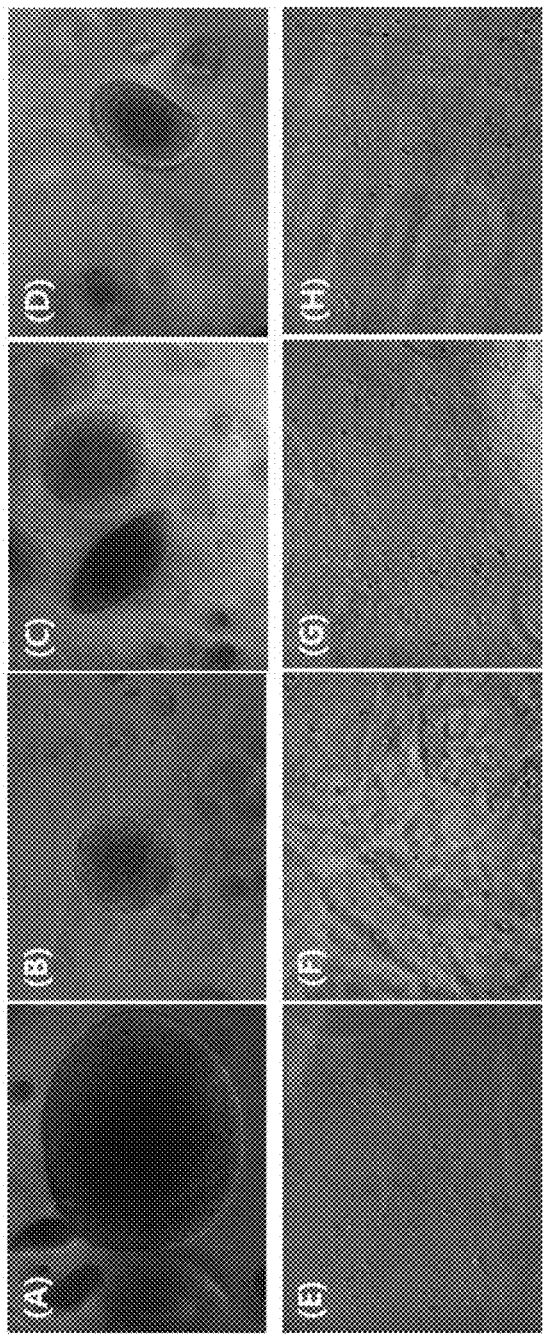
FIGS. 18A-18H. ReNcell VM after 2 Weeks of Proliferation and 2 Weeks of Differentiation (FIGS. 18A-18D) and after 4 weeks of differentiation (FIGS. 18E-18H). Alginate gels were formed with 5 mM (FIGS. 18A, 18E), 10 mM (FIGS. 18B, 18F), 50 mM (FIGS. 18C, 18G) and 100 mM (FIGS. 18D, 18H) of $CaCl_2$ solution.
Figure 19:
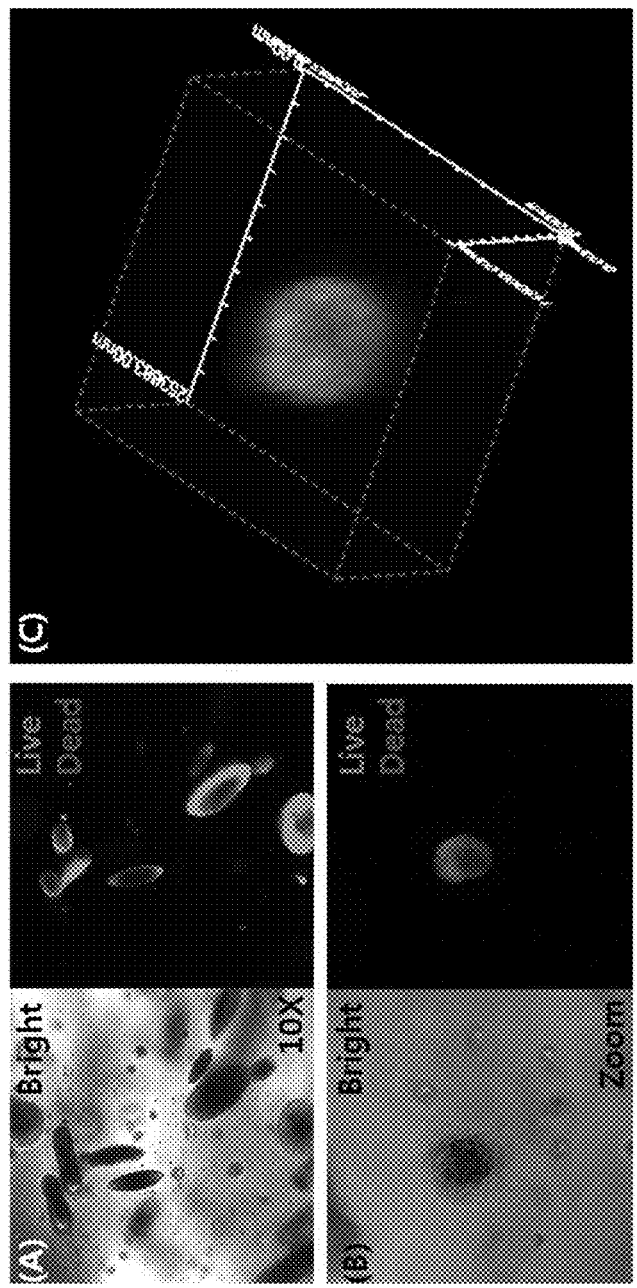
FIGS. 19A-19C. Live/dead Cell Assay Results of hNSCs Encapsulated in Calcium Alginate Hydrogels.
Figure 20:
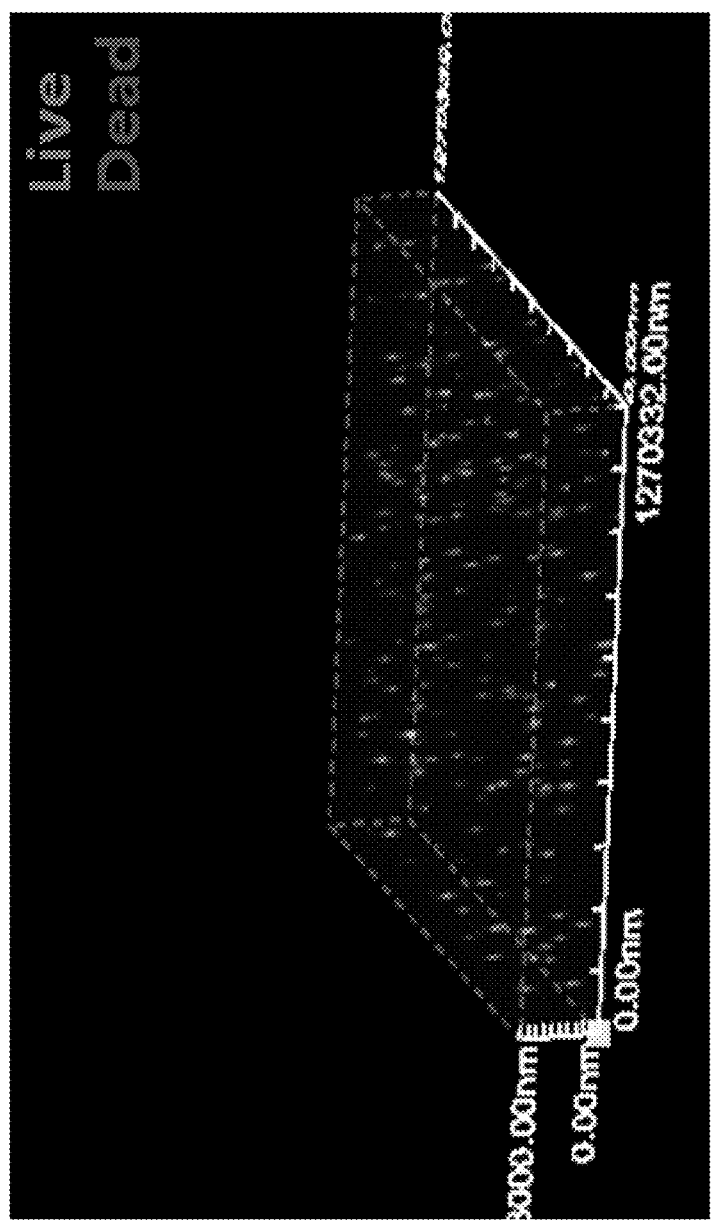
FIG. 20. 3D Reconstruction Image of 4-Week Differentiated Stem Cells inside Calcium Alginate Hydrogels. The differentiation process was started within one day of cell encapsulation.

3D tissue culture experiments were conducted to, first, assess how human neural stem cells survived in an encapsulated 3D culture microenvironment. Briefly, FIG. 18 shows two weeks of proliferation (growth factor treatment) of human neural stem cells (hNSCs; ReNcell VM, Millipore) in 3D hydrogels made up of calcium alginate that resulted in multiple neurospheres forming inside gel and exhibited good surviving viability. The proliferated hNSCs were cultured for 2 weeks with growth factor supplementation (i.e., bFGF, EGF) and differentiated for 4 weeks with growth factor-free stem cell media. After staining with calcein AM and ethidium homodimer-1 (EthD-1), the encapsulated neurospheres showed high cell viability (no Ethidium homodimer staining) (FIG. 19A). To investigate the cell viability inside neurosphere (which could be few hundred microns), Z-stack images were taken and the result showed no Ethidium homodimer staining inside the neurosphere, meaning no cell death inside (FIG. 19B). Based on the multiple files of Z-stack images, the 3D reconstruction of a single neurosphere stained with calcein AM was generated (FIG. 19C) and this rendered image showed no EthD-1-stained dead cells (no detectable red fluorescent signals). FIG. 20 shows the living hNSCs that were differentiated for 4 weeks right after the cells were encapsulated in calcium alginate. This shows that neural stem cell cultured in 3D alginate gel did not die inside the matrix for, at least, a month.

Cell Recovery (Decapsulation) after 3D Alginate Hydrogel Encapsulation

Figure 21:
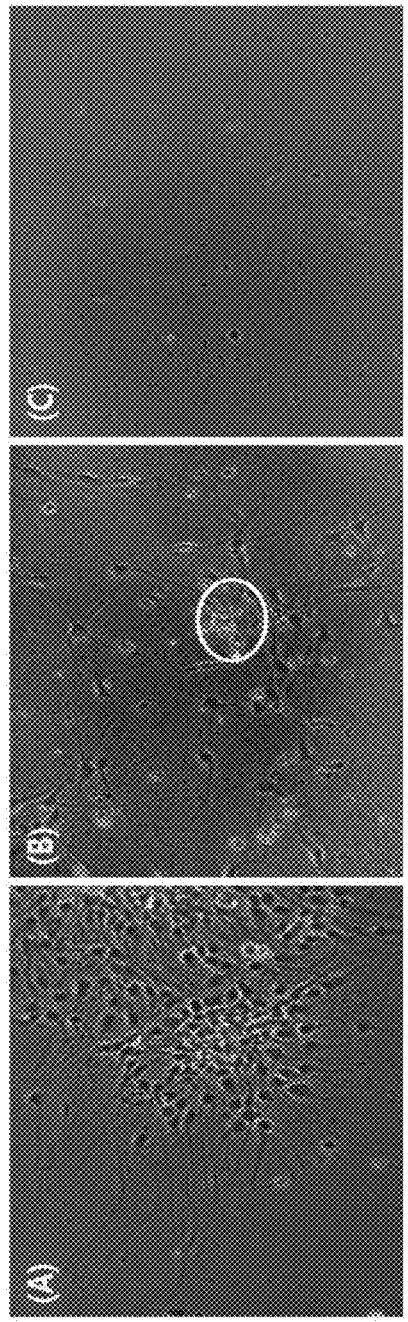
FIGS. 21A-21C. Microscopy Analysis of ReNcell VM cells after Decapsulation from 3D Calcium Alginate Hydrogels. hNSCs were (FIG. 21A) proliferated for 2 weeks, (FIG. 21B) proliferated for 2 weeks then differentiated for 2 weeks, and FIG. 21 (C) differentiated for 4 weeks inside gels. The cells highlighted in the white circle show detachment of cells leading to floating.

Experiments were designed to determine how to best recover ReNcell VM cells from 3D calcium alginate hydrogels so that the isolated cells can be used for gene expression studies via RT-qPCR. Citric acid which has three carboxylic acid groups can act as a chelating molecule for $Ca^{2+}$ ion. Using 100 mM of citric acid/PBS solution, cell decapsulation experiments were conducted and the cells were re-plated onto new laminin-coated surfaces. The isolated ReNcell VM cells that was subjected to growth factor-depleted differentiation methodology, however, exhibited poor binding propensities even to laminin-coated surfaces when plated without additional modifications (normally hNSCs can be cultured onto laminin without difficulty). These cells, however, needed to be transformed into neurospheres before they can bind well to laminin coated surfaces (FIG. 21).

Application of RA-PepB to 3D Encapsulated Neural Stem Cells and their Analysis

Figure 22:
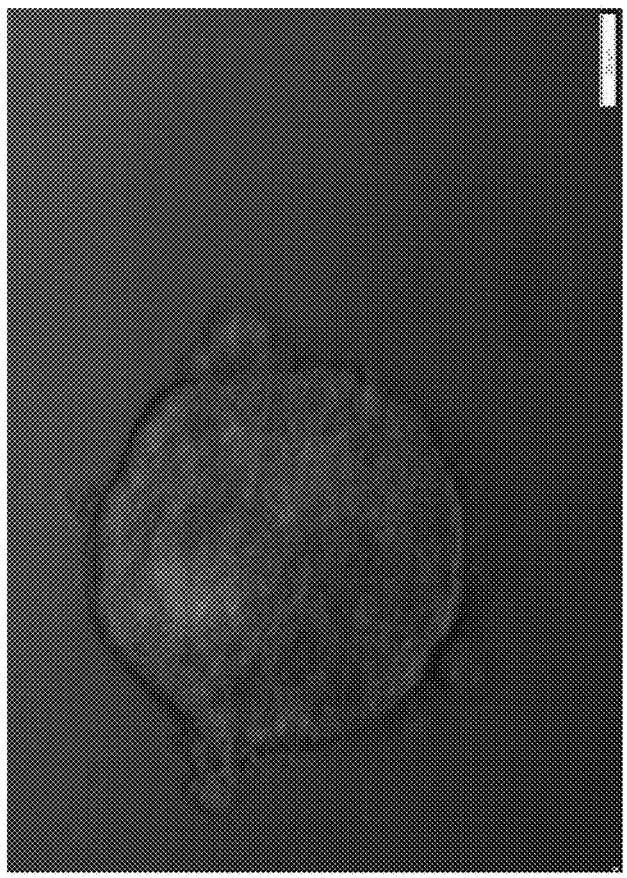
FIG. 22. Calcium Alginate Encapsulated hNSCs with Internalized Synthetic Peptide RA-PepB. 2 μM of RA-PepB (red) was treated to the hydrogel encapsulating hNSCs for one hour (40× Magnification).
Figure 23:
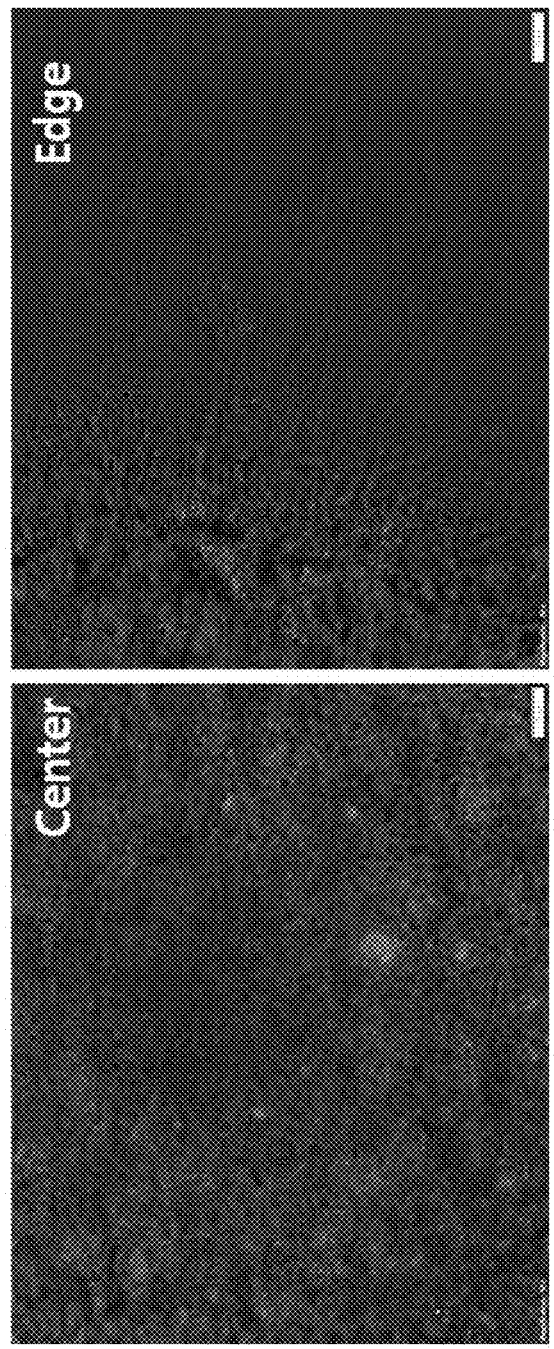
FIG. 23. RA-PepB Treated ReNcell VM Neurospheres in Calcium Alginate Hydrogels. RA-PepB incorporated hNSCs were decapsulated and seeded on the laminin-coated surfaces (60× Magnification).

Calcium Alginate Encapsulation:

After calcium alginate hydrogels were confirmed to be biocompatible with ReNcell VM cells, synthetic soluble factors such as RA-PepB, which has been shown to differentiate hNSCs into neurons, were tested inside the developed 3D hydrogels. RA-PepB (2 µM) was treated for one hour and RA-PepB molecules successfully internalized (FIG. 1). To confirm the cellular uptake of RA-PepB into ReNcell VM, the treated cells inside hydrogels were decapsulated and seeded onto laminin-coated 8 well chamber well slides. The live cell imaging results (FIG. 22, 23) show that RA-PepB molecules incorporated into ReNcell VM. These fluorescence microscopy results suggest that RA-PepB molecules entered and diffused into 3D calcium alginate hydrogels and finally internalized into ReNcell VM cells.

Methacrylated Hyaluronan

Figure 24:
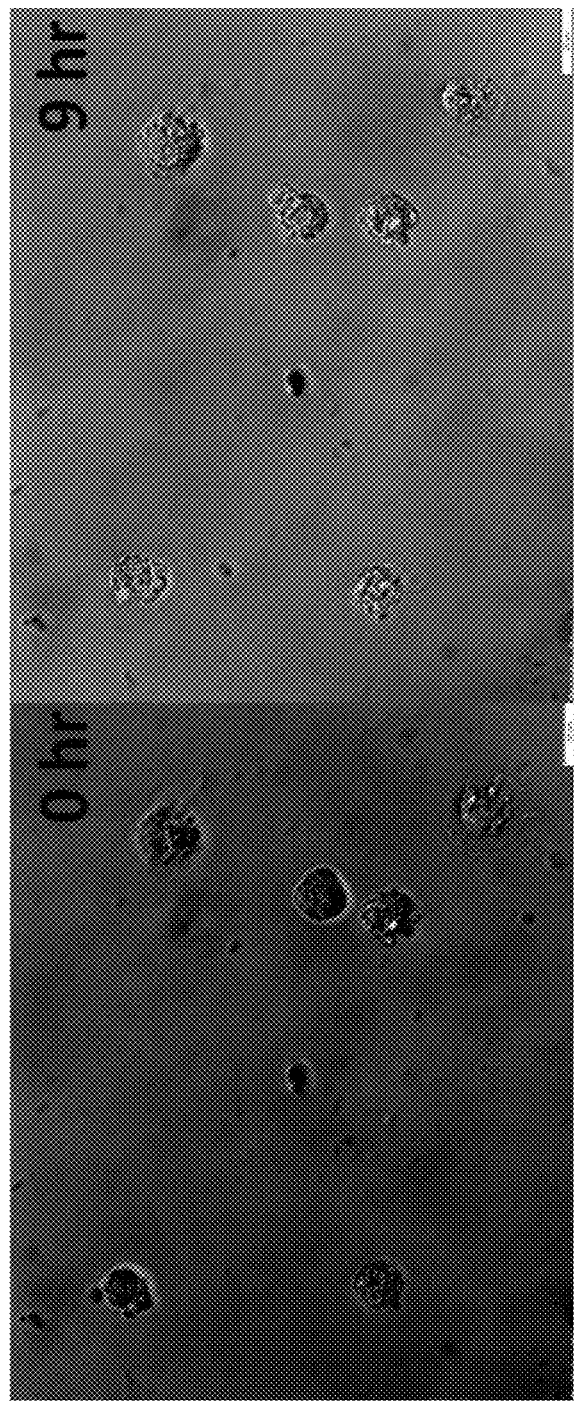
FIG. 24. RA-PepB (1 μM) Treated ReNcell VM Neurosphere in MeHA Gels. The cellular uptake images were taken over 9 hrs (20× magnification).
Figure 25:
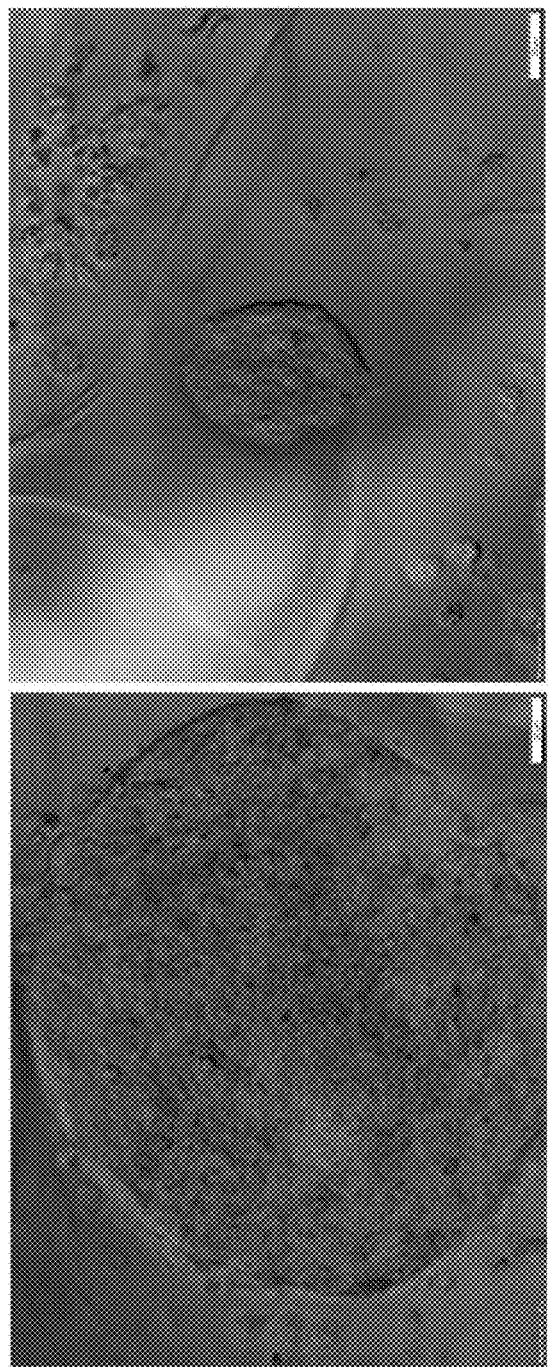
FIG. 25. ReNcell VM Cultured in MeHA Hydrogels. 2 μM of RA-PepB (red) was treated for 1 hr.
Figure 26:
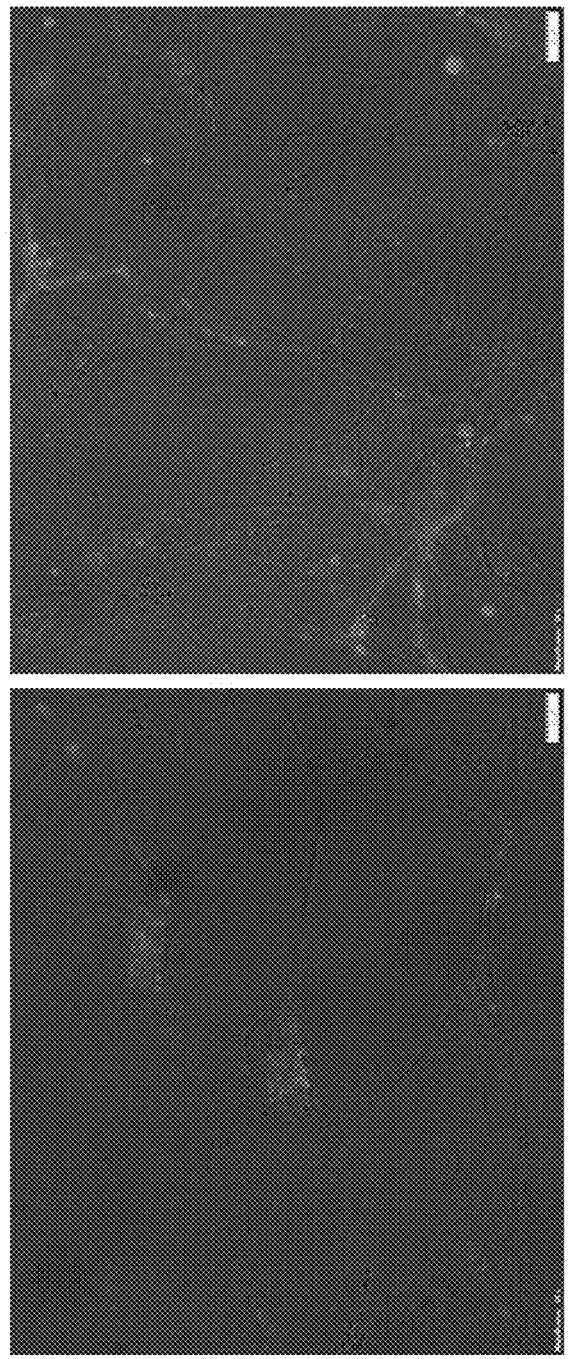
FIG. 26. Stem Cells Treated with RA-PepB Encapsulated in MeHA Hydrogels. The cells were grown and treated with RA-PepB inside MeHA hydrogels and then decapsulated onto laminin-treated surfaces. 2 μM of RA-PepB (red) was treated for 1 hr (60× magnification).

Photochemically crosslinked MeHA (methacrylated hyaluronan) hydrogels incorporating hNSCs were treated with RA-PepB molecules. RA-PepB internalized into ReNcell VM neurospheres encapsulated in MeHA gels. In another experiment, time-dependent cellular uptake of RA-PepB were monitored via time lapse imaging. It showed that it takes approximately 9 hours to internalize into 3D hydrogels and then the cells (FIG. 24). Only 2 hours of RA-PepB treatment was enough for the cellular uptake of RA-PepB to ReNcell VM. The cellular uptake of RA-PepB was observed in the neurosphere mode (FIG. 25) and the RA-PepB uptake was confirmed after decapsulation and re-seeding onto laminin-coated 2D surface (FIG. 26).

Calcium Alginate Encapsulated Neural Stem Cell Gene Expression Analysis

Figure 27:
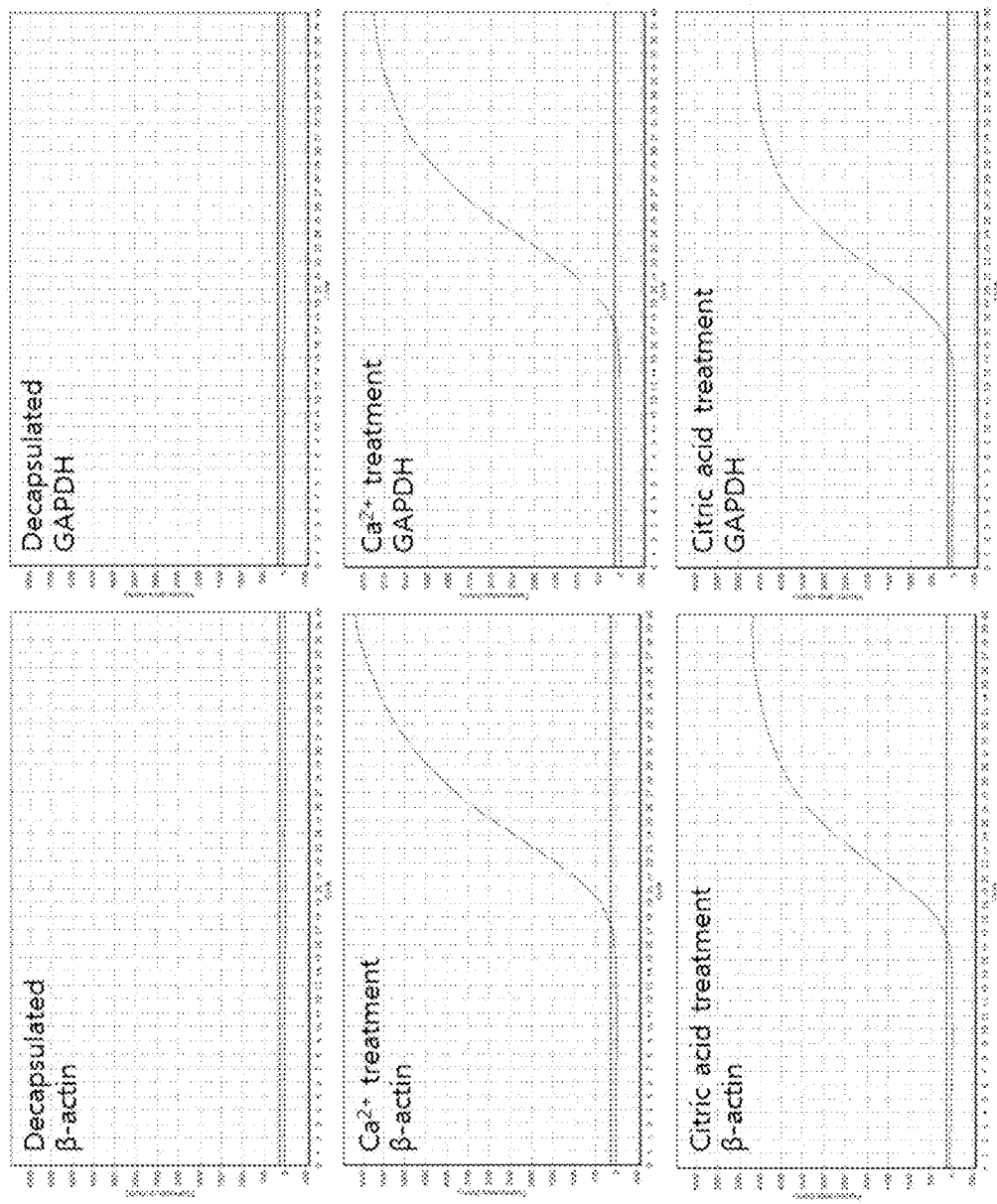
FIG. 27. mRNA Expression Profiles of House Keeping Genes. Isolated mRNAs were converted to cDNAs and then analyzed by real time PCR to understand the levels of β-actin and GAPDH.

To investigate the effect of RA-PepB uptake into ReNcell VM, the changes in the genetic expression can be analyzed, however, no Ct values were observed for the ReNcell VM samples after decapsulation. $Ca^{2+}$ and citric acid (metal ion chelator) can act as PCR inhibitors since $Mg^{2+}$ is the cofactor of Taq polymerase. RT-qPCR experiments were conducted after treatment of 100 mM of $Ca^{2+}$ and 100 mM of citric acid for 10 min. The results show that $Ca^{2+}$ and citric acid do not inhibit RT-qPCR (FIG. 27).

Figure 28:
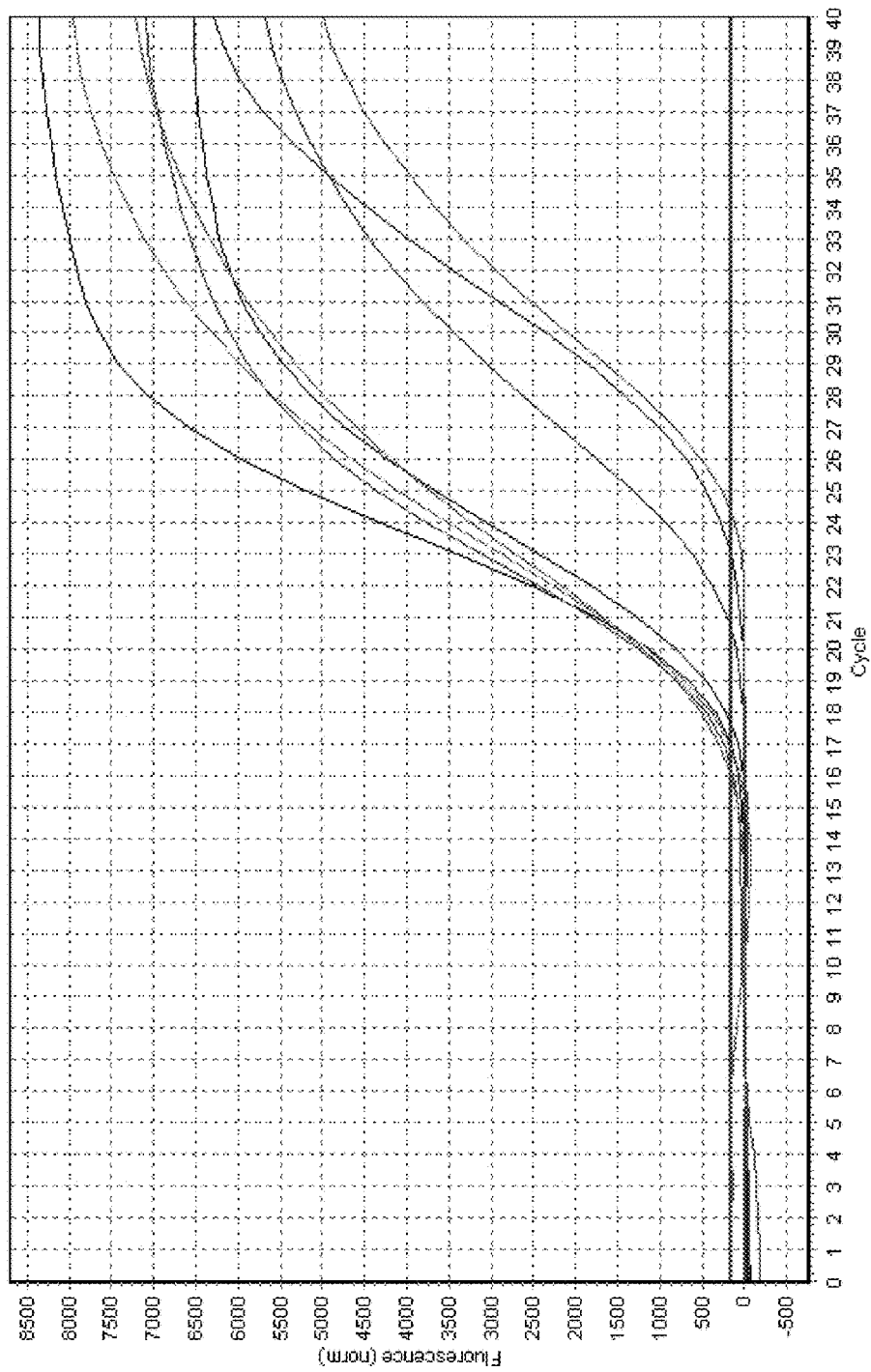
FIG. 28. mRNA Expression Profiles of Nestin, SOX2, Tubb3, MAP2, GFAP, OMG, β-actin, and GAPDH. Isolated mRNAs were converted to cDNAs and then analyzed by real time PCR to understand the levels. Specific $C_t$ values are as follows: Nestin=16.92, SOX2=17.64, Tubb3=22.89, MAP2=20.58, GFAP=16.28, OMG=24.34, β-actin=15.93, and GAPDH=16.89.
Figure 29:
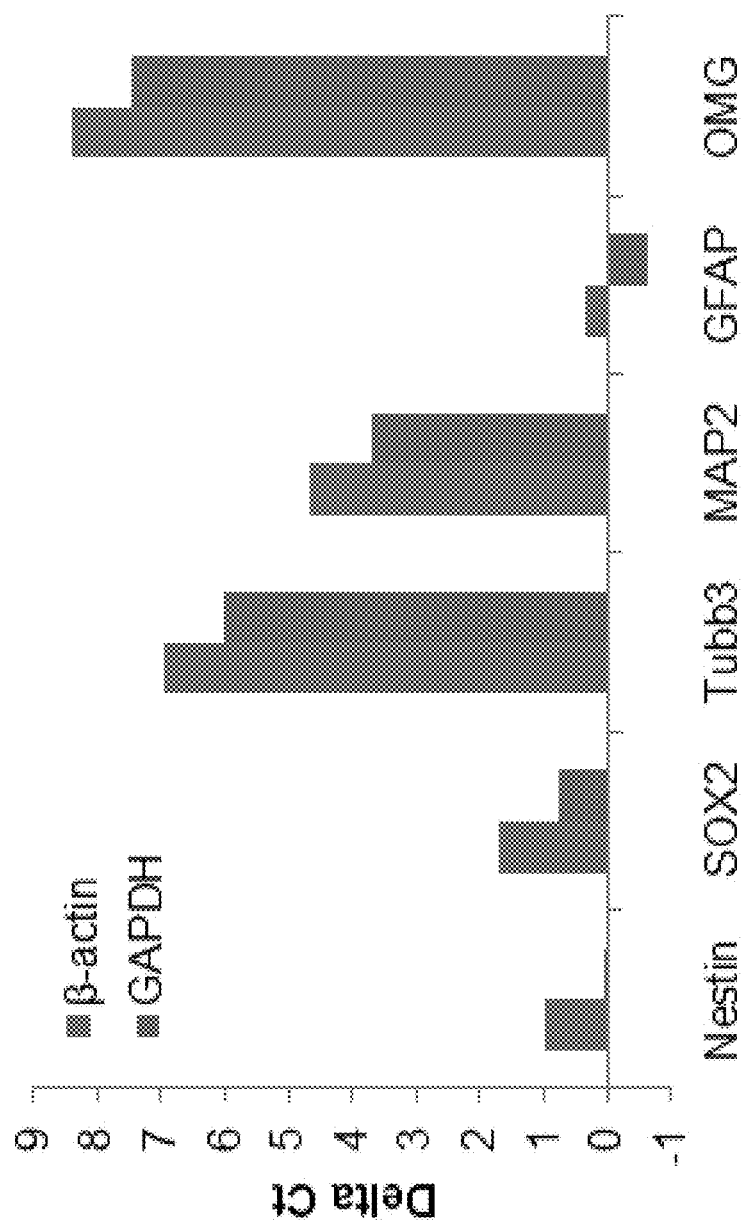
FIG. 29. Delta Ct Values for the Genetic Markers Nestin, SOX2, Tubb3, MAP2, GFAP, and OMG (relative to β-actin or GAPDH).

The next experiment was designed to, investigate alginate's potential inhibitory role in PCR by attempting to completely removing alginate (polysaccharide polymer) via extensively washing the decapsulated cells with citric acid (100 mM) and PBS before re-attachment. FIG. 28 shows the PCR plots having $C_t$ values for multiple genes were normally monitor to characterize hNSC differentiation. FIG. 29 shows delta $C_t$ value that more effectively shows expression level differences for nestin, SOX2, GFAP, Tubb3, MAP2, OMG relatively to house keeping genes ActB and GAPDH. The higher the delta Ct values are the lower the gene expression level for that gene. Using the same protocol, the effect of RA-PepB in 3D-grown ReNcell VM can be investigated.

Example 5: New Syntheses and MALDI Analysis of PepB Molecules

New synthesis was performed and the molecules were analyzed via MALDI. Chemical structures are provided in FIGS. 30A-30G.

Figure 30A:
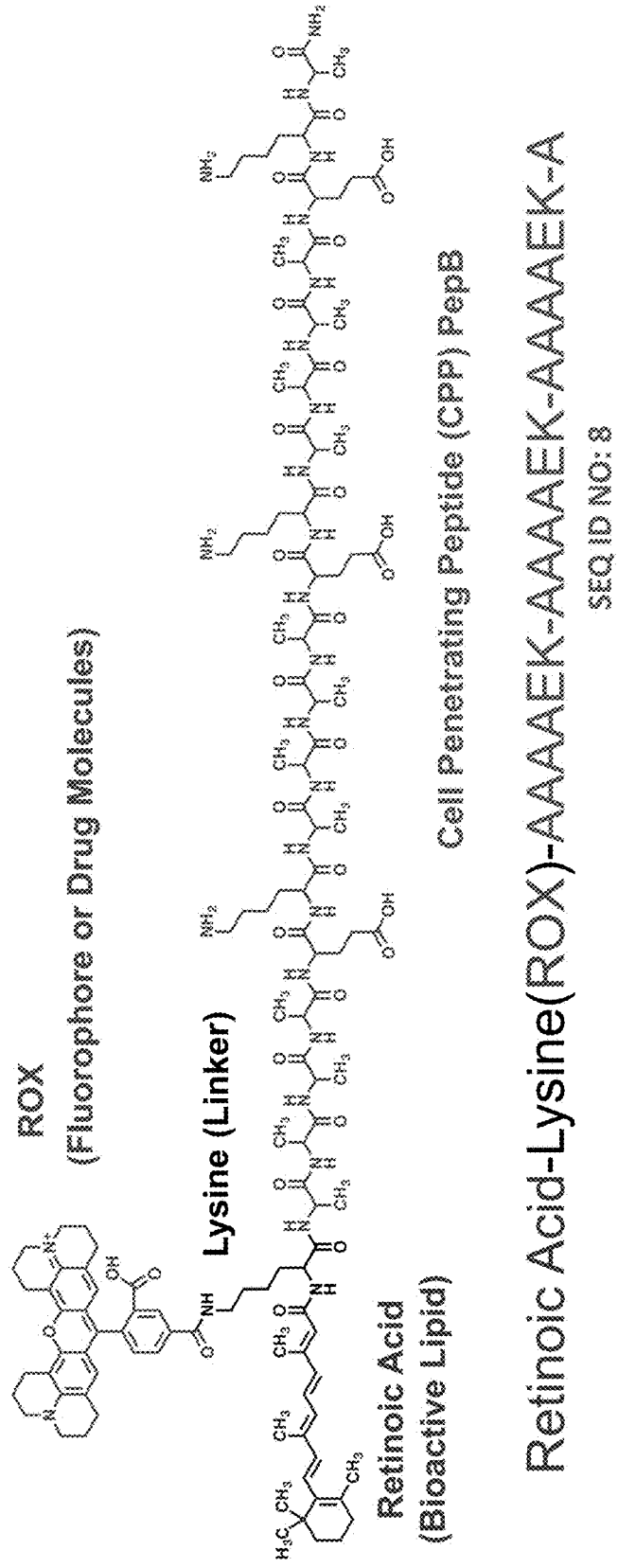
Figure 30B:
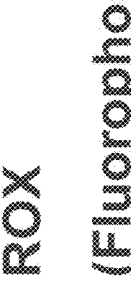
Figure 30C:
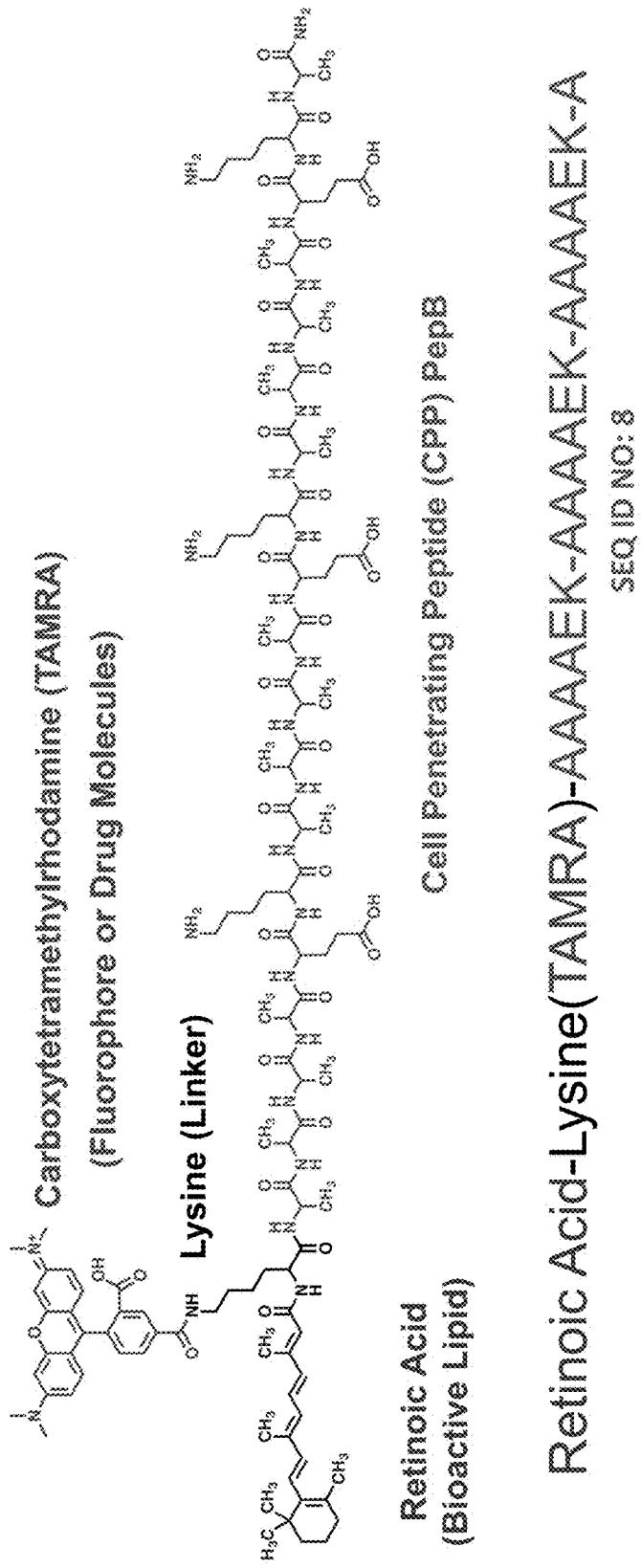
Figure 30E:
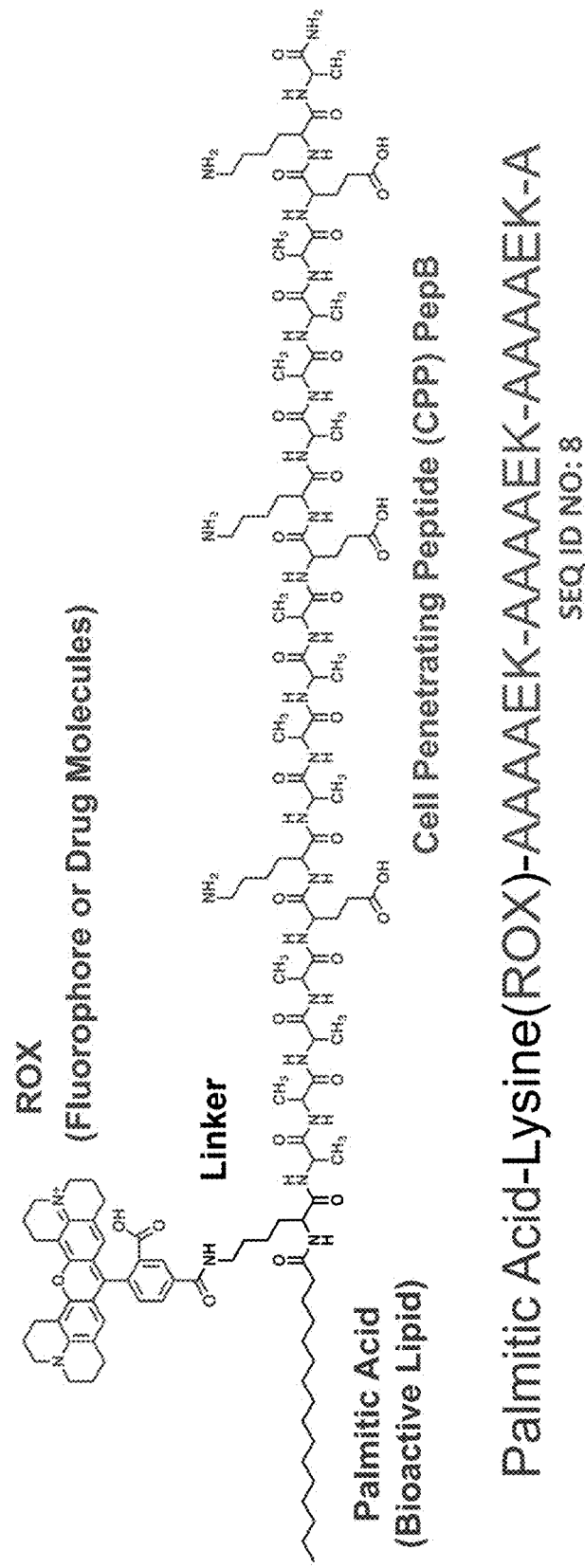

In one category, PepB can be appended with Retinoic Acid as the Hydrophobic Tail. For example, RA-PepB Labeled with the ROX Dye (FIG. 29A) and RA-PepB labeled with the TAMRA Dye (FIG. 30C).

Figure 30G:
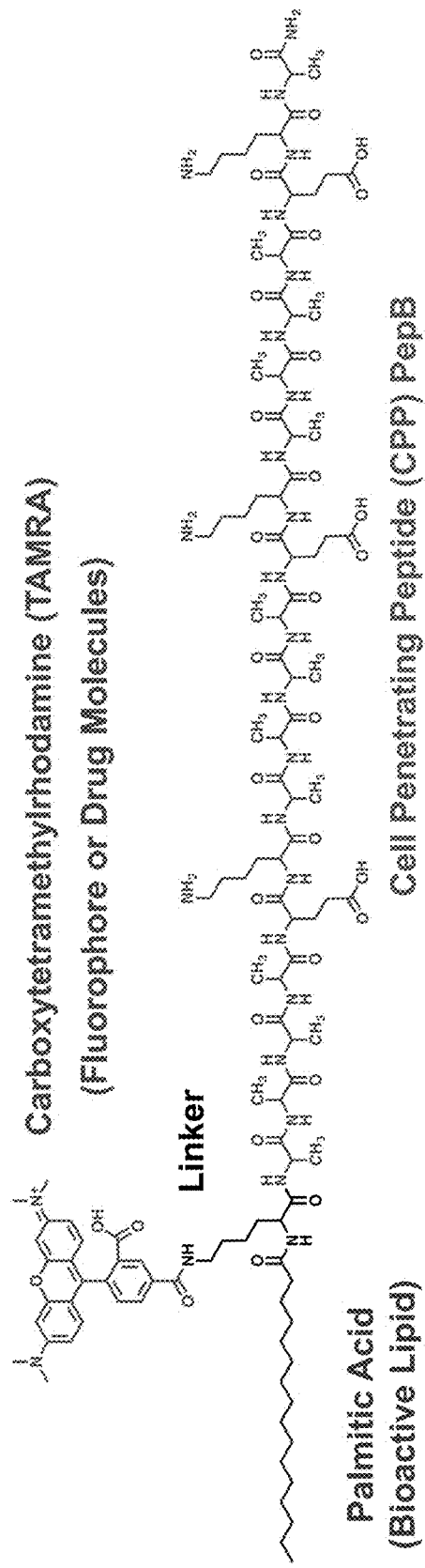

In another category, PepB can be appended with Palmitic Acid as the Hydrophobic Tail. For example, C16-PepB labeled with the ROX Dye (FIG. 30E) and C16-PepB labeled with the TAMRA Dye (FIG. 30G).

Figure 31A:
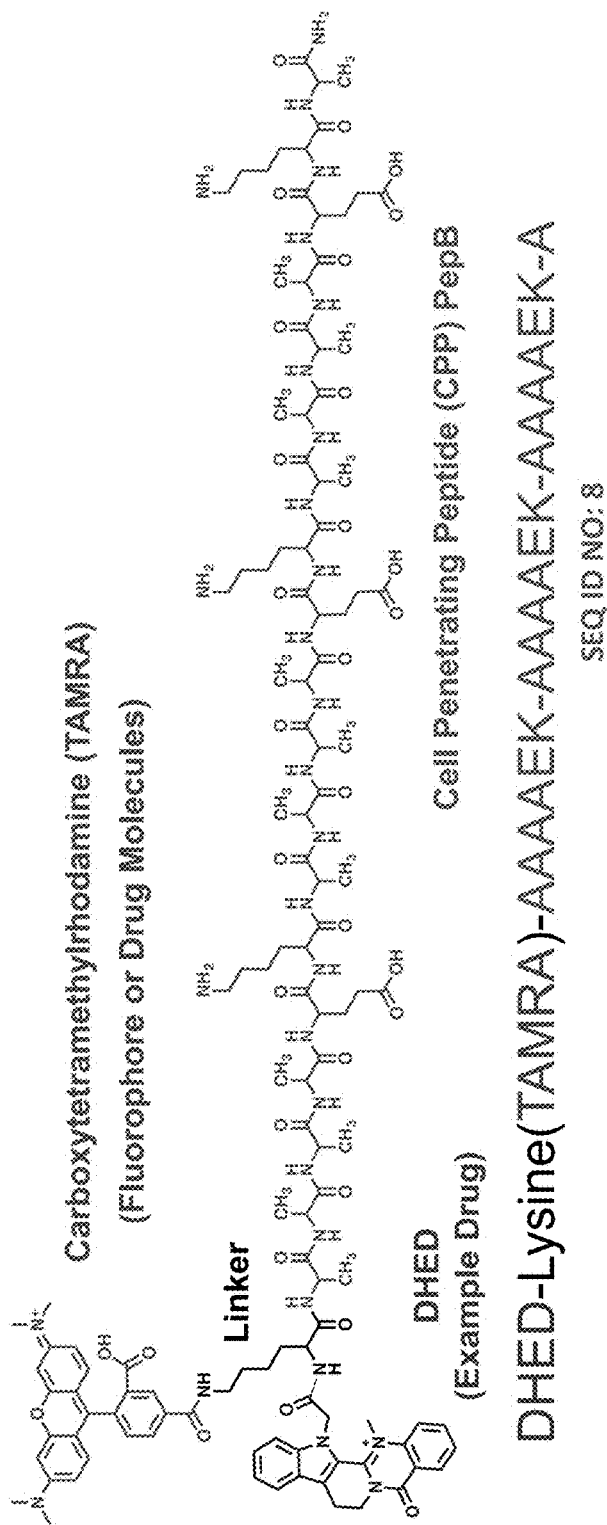
FIG. 31A depicts the chemical structure of DHED(TAMRA)PepB.

Example 6: New Synthetic PepB Constructs: PepB Construct Linked to a Hydrophobic Therapeutic Molecule Experiments can be designed to synthesis multifunctional molecules. The multifunctional molecules enable cell penetration, fluorescent labeling, and therapeutics delivery—all-in-one. Dehydroevodiamine (DHED) is a known Alzheimer's therapeutic small molecule and is, in addition, relatively hydrophobic so it is believed that the DHED (TAMRA)PepB molecule forms micellar constructs that can enhance the delivery and the efficacy of the incorporated drug molecule (FIG. 31A).

Example 7: Protein Expression of PepB

A cloning-based approach was designed to allow the incorporation of PepB moieties into biomacromolecules such as proteins. This, too, can produce multifunctional systems that enable cell penetration, fluorescent labeling, and/or therapeutics delivery—all-in-one. The plasmid vector design is as follows: (1) The genetic materials/codes for cell penetrating peptide (i.e., TAT or PepB) and GFP can be intercalated into pRSET or other identical vectors with restriction enzymes (i.e., BamH1 and EcoR1) and ligases, (2) synthetically prepared oligonucleotides (genetic sequences expressing PepB, specifically), after plasmid construction, can be transformed into bacteria and PepB-GFP can be expressed/produced.

FIG. 32A shows the entire DNA sequence of a representative DNA vector system. FIG. 32B shows a component analysis of the DNA vector system of FIG. 32A. Restriction enzyme cleavable sequences are designed as: [X] and [Y] (these will depend on the vector utilized). Insertion points: *. Additional sites to include nucleic acid codes depending on the vector map and specific need.

The genetic map presented in FIG. 32A represents the genetic sequence that can encode a fusion protein that incorporated the PepB sequence. The specific example shows PepB linked to EGFP (PepB-EGFP).

Restriction enzyme sites ([X], [Y]) can be positioned at the terminal sides (3' and 5') of the fusion protein genetic map. For instance, if the insertion vector was pRSET, X can be GGATCC and Y can be GAATTC and they can be utilized in combination with BamHI and EcoRI restriction enzymes, respectively. Both X and Y can be replaced by other sequences and examples include TGTACA (AaaI), GACGTC (AatII), TGATCA (AbaI), CTCGAG (AbrI), TCCGGA (AccII), GGTACC (Acc65I), CTCGAG (XhoI), AAGCTT (HindIII), CTGCA (PstI), CCCGGG (SmaI) depending on the restriction sites in pDNA (here the restriction enzymes are provided in the parentheses).

The linker (or spacer) between the genetic sequence for PepB and the target protein (i.e., EGFP) can be deleted or replaced with any other genetic sequence that encodes various peptide sequences. The spacer can be the restriction site. Basically, if a linker is inserted, the overall fusion protein will be PepB linked to the target protein via a spacer.

The provided sequence translates to a fusion protein (i.e., PepB-Gly6-EGFP) incorporating the PepB sequence on the N-terminus. The positioning of the PepB sequence can, in addition, be modified to be at the C-terminus side. Below is the fusion protein amino acid (single letter) sequence. This particular example shows the start codon becoming methionine and then PepB, Gly6, and EGFP are subsequently translated (FIG. 33A). The AAAAEK sequence can be repeated (or not repeated) multiple times. The number of AAAAEK sequences being repeating can be increased to potentially increase the cell penetrating efficiencies. The linker sequence can be of different length and combinations of available amino acids. The most common space choices can be hydrophobic amino acids with relatively smaller residues such as glycine, alanine, valine but not limited to them. The specific Gly6 example is chosen, first, since it is the least bulky peptide sequence and the linear peptide linker length can be somewhere between 0.5-3 nm (depending on the eventually secondary structure).

Although the present invention has been described in detail with reference to examples above, it is understood that various modifications can be made without departing from the spirit of the invention. Accordingly, the invention is limited only by the following claims. All cited patents and publications referred to in this application are herein incorporated by reference in their entirety.

What is claimed is:

1. A composition comprising a cell penetrating peptide (CPP), wherein the CPP comprises the sequence of AAAAEK (SEQ ID NO: 1) or a variant thereof, and wherein the composition comprises a terminal alanine after the sequence of SEQ ID NO: 1.

2. The composition of claim 1, wherein the CPP further comprises another sequence AAAAEK (SEQ ID NO: 1) at the N-terminus of the CPP.

3. The composition of claim 1, wherein the CPP is linked to a cargo.

4. The composition of claim 3, wherein the cargo is conjugated to the peptide at the N-terminus of the peptide.

5. The composition of claim 3, wherein the cargo is conjugated to the peptide at the C-terminus of the peptide.

6. The composition of claim 3, wherein the cargo molecule is selected from the group comprising a nucleic acid molecule, an amino acid molecule, a therapeutically active peptide, a protein, a carbohydrate, a lipid, a contrast or imaging agent, a quantum dot, a diagnostic agent, a therapeutic agent, and any combination thereof.

7. The composition of claim 3, wherein the cargo is selected from the group consisting of a cell homing peptide, an aptamer, a receptor ligand, a spacer comprising a cleavable site coupled to an inactivating peptide, a peptide ligand, a cytotoxic peptide, a bioactive peptide, an antibody, a protein, and any combination thereof.

8. A composition comprising a cell penetrating peptide (CPP), wherein the CPP comprises contiguously repeated sequence of AAAAEK (SEQ ID NO: 1) or a variant thereof.

* * * * *

SEQUENCE LISTING

<160> NUMBER OF SEQ ID NOS: 11

<210> SEQ ID NO 1
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 1

Ala Ala Ala Ala Glu Lys
1               5

<210> SEQ ID NO 2
<211> LENGTH: 11
<212> TYPE: PRT
<213> ORGANISM: Artificial Sequence
<220> FEATURE:
<223> OTHER INFORMATION: Model bioactive peptide A

<400> SEQUENCE: 2

Ala Ser Val Lys Glu Tyr Pro Ser Arg Asp Thr
1               5                   10

<210> SEQ ID NO 3
<211> LENGTH: 795
<212> TYPE: DNA
<213> ORGANISM: Artificial Sequence
<220> FEATURE:
<223> OTHER INFORMATION: DNA vector system

<400> SEQUENCE: 3
atggctgctg ctgctgaaaa agccgccgcc gccgagaagg cagcagcggc ggaaaaggcg      60
ggtggcggag ggggtggcgt gagcaagggc gaggagctgt tcaccggggt ggtgcccatc     120
ctggtcgagc tggacggcga cgtaaacggc cacaagttca gcgtgtccgg cgagggcgag     180
ggcgatgcca cctacggcaa gctgaccctg aagttcatct gcaccaccgg caagctgccc     240
gtgccctggc ccaccctcgt gaccaccctg acctacggcg tgcagtgctt cagccgctac     300
cccgaccaca tgaagcagca cgacttcttc aagtccgcca tgcccgaagg ctacgtccag     360
gagcgcacca tcttcttcaa ggacgacggc aactacaaga cccgcgccga ggtgaagttc     420
gagggcgaca ccctggtgaa ccgcatcgag ctgaagggca tcgacttcaa ggaggacggc     480
aacatcctgg ggcacaagct ggagtacaac tacaacagcc acaacgtcta tatcatggcc     540
gacaagcaga agaacggcat caaggtgaac ttcaagatcc gccacaacat cgaggacggc     600
agcgtgcagc tcgccgacca ctaccagcag aacaccccca tcggcgacgg ccccgtgctg     660
ctgcccgaca ccactacct gagcacccag tccgccctga gcaaagaccc caacgagaag     720
cgcgatcaca tggtcctgct ggagttcgtg accgccgccg ggatcactct cggcatggac     780
gagctgtaca agtaa                                                       795

<210> SEQ ID NO 4
<211> LENGTH: 57
<212> TYPE: DNA
<213> ORGANISM: Artificial Sequence
<220> FEATURE:
<223> OTHER INFORMATION: PepB sequence

<400> SEQUENCE: 4
gctgctgctg ctgaaaaagc cgccgccgcc gagaaggcag cagcggcgga aaaggcg         57

<210> SEQ ID NO 5
<211> LENGTH: 18
<212> TYPE: DNA
<213> ORGANISM: Artificial Sequence
<220> FEATURE:
<223> OTHER INFORMATION: Linker sequence

<400> SEQUENCE: 5
ggtggcggag ggggtggc                                                    18

<210> SEQ ID NO 6
<211> LENGTH: 717
<212> TYPE: DNA
<213> ORGANISM: Artificial Sequence
<220> FEATURE:
<223> OTHER INFORMATION: EGFP sequence

<400> SEQUENCE: 6

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg ccccaccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga cacccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg     660
ctggagttcg tgaccgccgc cgggatcact ctcggcatgg acgagctgta caagtaa      717
```

<210> SEQ ID NO 7
<211> LENGTH: 264
<212> TYPE: PRT
<213> ORGANISM: Artificial Sequence
<220> FEATURE:
<223> OTHER INFORMATION: sequence of PepB-Gly6-EGFP fusion protein

<400> SEQUENCE: 7

```
Met Ala Ala Ala Ala Glu Lys Ala Ala Ala Glu Lys Ala Ala Ala
1               5                   10                  15

Ala Glu Lys Ala Gly Gly Gly Gly Gly Gly Val Ser Lys Gly Glu Glu
            20                  25                  30

Leu Phe Thr Gly Val Val Pro Ile Leu Val Glu Leu Asp Gly Asp Val
        35                  40                  45

Asn Gly His Lys Phe Ser Val Ser Gly Glu Gly Glu Gly Asp Ala Thr
    50                  55                  60

Tyr Gly Lys Leu Thr Leu Lys Phe Ile Cys Thr Thr Gly Lys Leu Pro
65                  70                  75                  80

Val Pro Trp Pro Thr Leu Val Thr Thr Leu Thr Tyr Gly Val Gln Cys
                85                  90                  95

Phe Ser Arg Tyr Pro Asp His Met Lys Gln His Asp Phe Phe Lys Ser
            100                 105                 110

Ala Met Pro Glu Gly Tyr Val Gln Glu Arg Thr Ile Phe Phe Lys Asp
        115                 120                 125

Asp Gly Asn Tyr Lys Thr Arg Ala Glu Val Lys Phe Glu Gly Asp Thr
    130                 135                 140

Leu Val Asn Arg Ile Glu Leu Lys Gly Ile Asp Phe Lys Glu Asp Gly
145                 150                 155                 160

Asn Ile Leu Gly His Lys Leu Glu Tyr Asn Tyr Asn Ser His Asn Val
                165                 170                 175

Tyr Ile Met Ala Asp Lys Gln Lys Asn Gly Ile Lys Val Asn Phe Lys
```

180                 185                 190
Ile Arg His Asn Ile Glu Asp Gly Ser Val Gln Leu Ala Asp His Tyr
                195                 200                 205

Gln Gln Asn Thr Pro Ile Gly Asp Gly Pro Val Leu Leu Pro Asp Asn
            210                 215                 220

His Tyr Leu Ser Thr Gln Ser Ala Leu Ser Lys Asp Pro Asn Glu Lys
225                 230                 235                 240

Arg Asp His Met Val Leu Leu Glu Phe Val Thr Ala Ala Gly Ile Thr
                245                 250                 255

Leu Gly Met Asp Glu Leu Tyr Lys
            260

<210> SEQ ID NO 8
<211> LENGTH: 19
<212> TYPE: PRT
<213> ORGANISM: Artificial Sequence
<220> FEATURE:
<223> OTHER INFORMATION: model PepB sequence

<400> SEQUENCE: 8

Ala Ala Ala Ala Glu Lys Ala Ala Ala Ala Glu Lys Ala Ala Ala Ala
1               5                   10                  15

Glu Lys Ala

<210> SEQ ID NO 9
<211> LENGTH: 6
<212> TYPE: PRT
<213> ORGANISM: Artificial Sequence
<220> FEATURE:
<223> OTHER INFORMATION: Linker sequence

<400> SEQUENCE: 9

Gly Gly Gly Gly Gly Gly
1               5

<210> SEQ ID NO 10
<211> LENGTH: 238
<212> TYPE: PRT
<213> ORGANISM: Artificial Sequence
<220> FEATURE:
<223> OTHER INFORMATION: EGFP sequence

<400> SEQUENCE: 10

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

```
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
    210                 215                 220
Thr Ala Ala Gly Ile Thr Leu Gly Met Asp Glu Leu Tyr Lys
225                 230                 235

<210> SEQ ID NO 11
<211> LENGTH: 17
<212> TYPE: PRT
<213> ORGANISM: Artificial Sequence
<220> FEATURE:
<223> OTHER INFORMATION: Model PepA sequence

<400> SEQUENCE: 11

Ala Ala Ala Ala Glu Lys Ala Ser Val Lys Glu Tyr Pro Ser Arg Asp
1               5                   10                  15
Thr
```